US008685979B2

(12) United States Patent
Ren et al.

(10) Patent No.: US 8,685,979 B2
(45) Date of Patent: Apr. 1, 2014

(54) OLIGOMER-DIARYLPIPERAZINE CONJUGATES

(75) Inventors: Zhongxu Ren, Madison, AL (US); Jennifer Riggs-Sauthier, Huntsville, AL (US)

(73) Assignee: Nektar Therapeutics, San Francisco, CA (US)

(*) Notice: Subject to any disclaimer, the term of this patent is extended or adjusted under 35 U.S.C. 154(b) by 409 days.

(21) Appl. No.: 12/864,481

(22) PCT Filed: Jan. 22, 2009

(86) PCT No.: PCT/US2009/000475
§ 371 (c)(1),
(2), (4) Date: Sep. 16, 2011

(87) PCT Pub. No.: WO2009/094209
PCT Pub. Date: Jul. 30, 2009

(65) Prior Publication Data
US 2012/0004242 A1   Jan. 5, 2012

Related U.S. Application Data

(60) Provisional application No. 61/062,330, filed on Jan. 25, 2008.

(51) Int. Cl.
*A61K 31/495* (2006.01)
*C07D 241/04* (2006.01)

(52) U.S. Cl.
USPC ................ 514/252.12; 544/358; 544/399

(58) Field of Classification Search
USPC ................ 544/358, 398, 399; 514/252.12
See application file for complete search history.

(56) References Cited

U.S. PATENT DOCUMENTS

| 5,574,159 | A | * | 11/1996 | Chang et al. ............... 544/396 |
| 5,658,908 | A | | 8/1997 | Chang et al. |
| 5,672,662 | A | | 9/1997 | Harris et al. |
| 5,854,249 | A | * | 12/1998 | Chang et al. ............. 514/252.13 |
| 2005/0136031 | A1 | | 6/2005 | Bentley et al. |

FOREIGN PATENT DOCUMENTS

| GB | 817231 | 1/1957 |
| WO | WO 02/098949 | 12/2002 |
| WO | WO 2008/112257 | 9/2008 |
| WO | WO 2008/112286 | 9/2008 |

OTHER PUBLICATIONS

Chang et al (1994): STN International HCAPLUS database, (Columbus, Ohio), Accession No. 1994: 483367.*
Bishop, et al., "An Efficient Synthesis of the Benzhydrylpiperazine Delta Opioid Agonist (+)-BW373U86," Bioorg. & Med. Chem. Lett., vol. 5, No. 12, pp. 1311-1314, (1995).
Brandt, et al., "Antinociceptive Effects of δ-Opioid Agonists in Rhesus Monkeys: Effects on Chemically Induced Thermal Hypersensitivity," The J. of Pharmacol. and Exper. Therap., vol. 296, No. 3, pp. 939-946, (2001).
Calderon, et al., "Probes for Narcotic Receptor Mediated Phenomena . . . ," J. Med. Chem., vol. 37, pp. 2125-2128, (1994).
Chang, et al., "A Novel, Potent and Selective Nonpeptidic Delta Opioid Receptor Agonist BW373U86," The J. of Pharmacol. and Exper. Therap., vol. 267, No. 2, pp. 852-857, (1993).
Chang, et al., "Multiple Opiate Receptors," The J. of Biol. Chem., Issue of Apr. 25, vol. 254, No. 8, pp. 2610-2618, (1979).
Chang, et al., "Multiple Opiate Receptors: Different Regional Distribution in the Brain and Differential Binding of Opiates and Opioid Peptides," Molecular Pharmacol., vol. 16, pp. 91-104, (1979).
Chen, et al., "Synthesis and Properties of ABA Amphiphiles," J. Org. Chem., vol. 64, pp. 6870-6873, (1999).
Childers, et al., "BW373U86: A Nonpeptidic δ-Opioid Agonist with Novel Receptor-G Protein-Mediated Actions in Rat Brain Membranes and Neuroblastoma Cells," Molecular Pharmacol., vol. 44, pp. 827-834, (1993).
Comer, et al., "Convulsive Effects of Systemic Administration of the Delta Opioid Agonist BW373U86 in Mice," The J. of Pharmacol. and Exper. Therap., vol. 267, No. 2, pp. 888-895, (1993).
Comer, et al., "Discriminative Stimulus Effects of BW373U86: A Nonpeptide Ligand with Selectivity for Delta Opioid Receptors," The J. of Pharmacol. and Exper. Therap., vol. 267, No. 2, pp. 866-874, (1993).
Dykstra, et al., "A Novel Delta Opioid Agonist, BW373U86, in Squirrel Monkeys Responding under a Schedule of Shock Titration," The J. of Pharmacol. and Exper. Therap., vol. 267, No. 2, pp. 875-882, (1993).
Ertl, et al., "Fast Calculation of Molecular Polar Surface Area as a Sum of Fragment-Based Contributions and Its Application to the Prediction of Drug Transport," J. Med. Chem., vol. 43, pp. 3714-3717, (2000).
Kelder, et al., "Polar Molecular Surface as a Dominating Determinant for Oral Absorption and Brain Penetration of Drugs," Pharmaceu. Res., vol. 16, No. 10, pp. 1514-1519, (1999).
Lee, et al., "A Nonpeptidic Delta Opioid Receptor Agonist, BW373U86, Attenuates the Development and Expression of Morphine . . . ," The J. of Pharmacol. and Exper. Therap., vol. 267, No. 2, pp. 883-887, (1993).
Meindl, "Antimycobacterial Properties of Antihistaminic Compounds," Archiv Der Pharmazie (Weinheim), vol. 321, No. 8, pp. 473-476, (1988).
Negus, et al., "Behavioral Effects of the Delta-Selective Opioid Agonist SNC80 and Related Compounds in Rhesus Monkeys," The J. of Pharmacol. and Exper. Therap., vol. 286, No. 1, pp. 362-375, (1998).
O'Neill, et al., "Antagonistic Modulation Between the Delta Opioid Agonist BW373U86 and the Mu Opioid Agonist Fentanyl in Mice," The J. of Pharmacol. and Exper. Therap., vol. 282, No. 1, pp. 271-277, (1997).

(Continued)

*Primary Examiner* — Golam M M Shameem
(74) *Attorney, Agent, or Firm* — Mark A. Wilson

(57) ABSTRACT

The invention relates to (among other things) oligomer-diarylpiperazine conjugates and related compounds. A conjugate of the invention, when administered by any of a number of administration routes, exhibits advantages over previously administered un-conjugated diarylpiperazine compounds.

12 Claims, 2 Drawing Sheets

(56) References Cited

OTHER PUBLICATIONS

Wild, et al., "Antinociceptive Actions of BW373U86 in the Mouse," The J. of Pharmacol. and Exper. Therap., vol. 267, No. 2, pp. 858-865, (1993).
European Examination Report corresponding to European Patent Application No. 09 704 271.7 dated Feb. 28, 2011.
PCT International Search Report corresponding to PCT Application No. PCT/US2009/000475 date of mailing May 28, 2009.
PCT International Preliminary Report on Patentability corresponding to PCT Application No. PCT/US2009/000475 date of mailing Aug. 5, 2010.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005—2006).
NOF Corporation, PEG Derivatives, Phospholipid and Drug Delivery Materials for Pharmaceuticals, pp. 1-46, Catalogue 2003—1st, (Jan. 2003).
NOF Corporation, PEG Derivatives, Phospholipid and Drug Delivery Materials for Pharmaceuticals, pp. 1-50, Catalogue 2003—2nd, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, LTD., Leading innovator, producer and provider of monodisperse discrete PEG™ (dPEG™) derivatives, (Product Catalog), pp. 1-51, (Updated: Jul. 18, 2005).
Quanta Biodesign, LTD., Leading innovator, producer and provider of monodisperse discrete Pegtm (dPEG™) derivatives, (Product Catalog), pp. 1-51, (Updated: Nov. 17, 2005).
Shearwater Polymers, Inc., Polyethylene Glycol and Derivatives, 50 pages, (Catalog—Mar. 1995).
Shearwater Polymers, Inc., Polyethylene Glycol and Derivatives, 55 pages, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
European Communication corresponding to European Patent Application No. 09 704 271.7 dated Jun. 12, 2013.

* cited by examiner

OLIGOMER-DIARYLPIPERAZINE CONJUGATES

CROSS REFERENCE TO RELATED APPLICATIONS

This application is a 35 U.S.C. §371 application of International Application No. PCT/US2009/000475, filed 22 Jan. 2009, designating the United States, which claims the benefit of priority under 35 U.S.C. §119(e) to U.S. Provisional Patent Application Ser. No. 61/062,330, filed 25 Jan. 2008, both of which are incorporated herein by reference in their entireties.

FIELD OF THE INVENTION

This invention comprises (among other things) chemically modified opioid diarylpiperazines that possess certain advantages over opioid diarylpiperazines lacking the chemical modification. The chemically modified opioid diarylpiperazines described herein relate to and/or have application(s) in (among others) the fields of drug discovery, pharmacotherapy, physiology, organic chemistry and polymer chemistry.

BACKGROUND OF THE INVENTION

Opioid drugs, such as morphine, have long been used to treat patients suffering from pain. Opioid drugs exert their analgesic and other pharmacological effects through interactions with opioid receptors: mu (μ) receptors, kappa (κ) receptors, delta (δ) receptors, and sigma (σ) receptors.

The well-known narcotic opiates, such as morphine and its analogs, are selective for the opiate mu receptor. Mu receptors mediate analgesia, respiratory depression, and inhibition of gastrointestinal transit. Kappa receptors mediate analgesia and sedation. Sigma receptors mediate various biological activities.

The existence of the opioid delta receptor is a recent discovery which followed the isolation and characterization of endogenous enkephalin peptides which are ligands for the delta receptor. Research has produced significant information about the delta receptor, but a clear understanding of its function has not yet emerged. Delta receptors mediate analgesia, but do not appear to inhibit intestinal transit in the manner characteristic of mu receptors.

Pharmacologically, opioid drugs represent a class of agents employed in the management of pain, and also in combating drug addiction, alcohol addiction, drug overdose, mental illness, urinary incontinence, cough, lung edema, diarrhea, depression, and cognitive, respiratory, and gastro-intestinal disorders. Unfortunately, the use of opioid drugs is associated with the potential for abuse. In addition, oral administration of opioid drugs often results in significant first pass metabolism. Furthermore, administration of opioid drugs results in significant CNS-mediated effects, such as slowed breathing, which may result in death. Thus, a reduction of any one of these or other characteristics would enhance their desirability as therapeutic agents.

Recently, a class of potent and selective delta opioid receptor binding agents, diarylpiperazines (including compound BW373U86), has been described (See U.S. Pat. No. 5,658,908, and Chang, K. J., et al.; J. Pharmacol. Exp. Ther. 267, 852-857 (1993)). However, preliminary experiments have suggested that BW373U86 may produce an increase in hyperactivity, including convulsions (Corner, S., et al; J. Pharmacol. Exp. Ther. 267, 888-895 (1993)). Therefore, pharmacotherapy with opioid diarylpiperazines would be improved if these and/or other side effects associated with their use could be decreased or if their pharmacology could be improved. Thus, there is a large unmet need for developing novel opioid diarylpiperazine compounds.

The present invention seeks to address these and other needs in the art.

SUMMARY OF THE INVENTION

In one or more embodiments of the invention, a compound is provided, the compound comprising an opioid diarylpiperazine residue covalently attached via a stable or degradable linkage to a water-soluble, non-peptidic oligomer.

Exemplary compounds of the invention include those having the following structure:

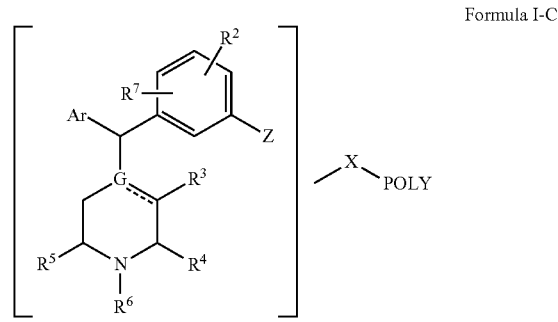

Formula I-C wherein:
Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined at a ring carbon atom (i.e., at a ring carbon atom of Ar);
Y is selected from the group consisting of:
hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;
sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;
sulfones of the formula $SO_2R^8$ where $R^8$ is the same as above; nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl; carboxamides of the formula $CONR^9R^{10}$ where $R^9$ and $R^{10}$ are the same as above;
sulfonamides of the formula $SO_2NR^9R^{10}$ where $R^9$ and $R^{10}$ are the same as above; and
$CONR^9AB$, where:
A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and
B is a dimer-forming moiety which is joined to a first valence bond of the divalent ligand A, and which is symmetric about the divalent ligand A to the compound moiety joined to the other valence bond of the divalent ligand A;

Z is selected from the group consisting of hydroxyl, and acyl esters thereof whose acyl moiety is selected from the group consisting of $CH_3CO$, $C_6H_5CO$, $(CH_3)_2NCO$, and $Me_3CCO$; hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;
$R^1$ is hydrogen, halogen, or $C_1$-$C_4$;
$R^2$ is hydrogen, halogen, or $C_1$-$C_4$;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;
$R^6$ is selected from the group consisting of hydrogen; $C_1$-$C_6$ alkyl; $C_3$-$C_6$ cycloalkyl; allyl; 2-buten-1-yl; 2-methyl-2-propen-1-yl; 2-chloro-2-propen-1-yl; alkoxyalkyl having $C_1$-$C_4$ alkoxy and $C_1$-$C_4$ alkyl moieties; $C_2$-$C_4$ cyanoalkyl; $C_2$-$C_4$ hydroxyalkyl; aminocarbonylalkyl having a $C_1$-$C_4$ alkyl moiety; alkylaryl having $C_1$-$C_4$ alkylene and $C_6$-$C_{14}$ aryl moieties; and $R^{12}COR^{13}$, where $R^{12}$ is $C_1$-$C_4$ alkylene, and $R^{13}$ is $C_1$-$C_4$ alkyl or $C_1$-$C_4$ alkoxy;
$R^7$ is hydrogen or fluorine, subject to the proviso that: $R^1$, $R^2$ and $R^7$ may be fluorine only when Z is —OH;
X is a spacer moiety, and is covalently attached to an atom; and
POLY is a water-soluble, non-peptidic oligomer.

Further exemplary compounds include those having the following structure:

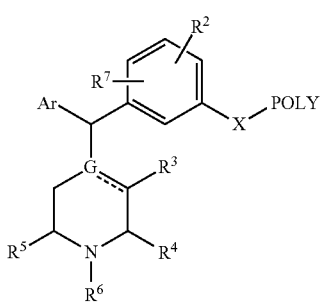

Formula Ia-C wherein:
Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined at a ring carbon atom (i.e., at a ring carbon atom of Ar);
Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;
sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;
sulfones of the formula $SO_2R^8$ where $R^8$ is the same as above; nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl;
carboxamides of the formula $CONR^9R^{10}$ where $R^9$ and $R^{10}$ are the same as above;
sulfonamides of the formula $SO_2NR^9R^{10}$ where $R^9$ and $R^{10}$ are the same as above; and
$CONR^9AB$, where:
A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and
B is a dimer-forming moiety which is joined to a first valence bond of the divalent ligand A, and which is symmetric about the divalent ligand A to the compound moiety joined to the other valence bond of the divalent ligand A;
G is nitrogen;
$R^1$ is hydrogen, halogen, or $C_1$-$C_4$;
$R^2$ is hydrogen, halogen, or $C_1$-$C_4$;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;
$R^6$ is selected from the group consisting of hydrogen; $C_1$-$C_6$ alkyl; $C_3$-$C_6$ cycloalkyl; allyl; 2-buten-1-yl; 2-methyl-2-propen-1-yl; 2-chloro-2-propen-1-yl; alkoxyalkyl having $C_1$-$C_4$ alkoxy and $C_1$-$C_4$ alkyl moieties; $C_2$-$C_4$ cyanoalkyl; $C_2$-$C_4$ hydroxyalkyl; aminocarbonylalkyl having a $C_1$-$C_4$ alkyl moiety; alkylaryl having $C_1$-$C_4$ alkylene and $C_6$-$C_{14}$ aryl moieties; and $R^{12}COR^{13}$, where $R^{12}$ is $C_1$-$C_4$ alkylene, and $R^{13}$ is $C_1$-$C_4$ alkyl or $C_1$-$C_4$ alkoxy;
$R^7$ is hydrogen or fluorine;
X is a spacer moiety; and
POLY is a water-soluble, non-peptidic oligomer.

Exemplary compounds include those having the following structure:

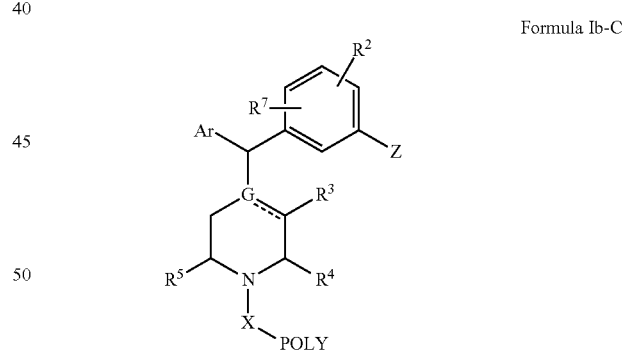

Formula Ib-C wherein:
Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined at a ring carbon atom (i.e., at a ring carbon atom of Ar);
Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;
sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;

sulfones of the formula $SO_2R^8$ where $R^8$ is the same as above; nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl; carboxamides of the formula $CONR^9R^{10}$ where $R^9$ and $R^{10}$ are the same as above;

sulfonamides of the formula $SO_2NR^9R^{10}$ where $R^9$ and $R^{10}$ are the same as above; and $CONR^9AB$, where:

A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of hydroxyl, and acyl esters thereof whose acyl moiety is selected from the group consisting of $CH_3CO$, $C_6H_5CO$, $(CH_3)_2NCO$, and $Me_3CCO$; hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;

$R^1$ is hydrogen, halogen, or $C_1$-$C_4$;

$R^2$ is hydrogen, halogen, or $C_1$-$C_4$;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^7$ is hydrogen or fluorine, subject to the proviso that: $R^1$, $R^2$ and $R^7$ may be fluorine only when Z is —OH;

X is a spacer moiety; and

POLY is a water-soluble, non-peptidic oligomer.

The "opioid diarylpiperazine residue" is a compound having a structure of an opioid diarylpiperazine compound that is altered by the presence of one or more bonds, which bonds serve to attach (either directly or indirectly) one or more water-soluble, non-peptidic oligomers.

In this regard, any diarylpiperazine compound having opioid delta receptor binding activity can be used as an opioid diarylpiperazine moiety. Exemplary opioid diarylpiperazine moieties have a structure encompassed by Formula I:

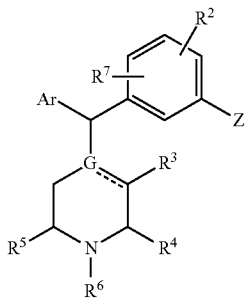

Formula I wherein:

Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined to the compound at a ring carbon atom of the Ar ring;

Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;

sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;

sulfones of the formula $SO_2R^8$ where $R^8$ is the same as above; nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl; carboxamides of the formula $CONR^9R^{10}$ where $R^9$ and $R^{10}$ are the same as above;

sulfonamides of the formula $SO_2NR^9R^{10}$ where $R^9$ and $R^{10}$ are the same as above; and $CONR^9AB$, where:

A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of hydroxyl, and acyl esters thereof whose acyl moiety is selected from the group consisting of $CH_3CO$, $C_6H_5CO$, $(CH_3)_2NCO$, and $Me_3CCO$; hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;

$R^1$ is hydrogen, halogen, or $C_1$-$C_4$;

$R^2$ is hydrogen, halogen, or $C_1$-$C_4$;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of hydrogen; $C_1$-$C_6$ alkyl; $C_3$-$C_6$ cycloalkyl; allyl; 2-buten-1-yl; 2-methyl-2-propen-1-yl; 2-chloro-2-propen-1-yl; alkoxyalkyl having $C_1$-$C_4$ alkoxy and $C_1$-$C_4$ alkyl moieties; $C_2$-$C_4$ cyanoalkyl; $C_2$-$C_4$ hydroxyalkyl; aminocarbonylalkyl having a $C_1$-$C_4$ alkyl moiety; alkylaryl having alkylene and $C_6$-$C_{14}$ aryl moieties; and $R^{12}COR^{13}$, where $R^{12}$ is $C_1$-$C_4$ alkylene, and $R^{13}$ is $C_1$-$C_4$ alkyl or $C_1$-$C_4$ alkoxy; and $R^7$ is hydrogen or fluorine, subject to the proviso that: $R^1$, $R^2$ and $R^7$ may be fluorine only when Z is —OH.

In one or more embodiments of the invention, a composition is provided, the composition comprising a compound comprising an opioid diarylpiperazine residue covalently attached via a stable or degradable linkage to a water-soluble, non-peptidic oligomer, and optionally, a pharmaceutically acceptable excipient.

In one or more embodiments of the invention, a dosage form is provided, the dosage form comprising a compound comprising an opioid diarylpiperazine residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to an opioid diarylpiperazine moiety.

In one or more embodiments of the invention, a method is provided, the method comprising administering a compound comprising an opioid diarylpiperazine residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

Figure 1:
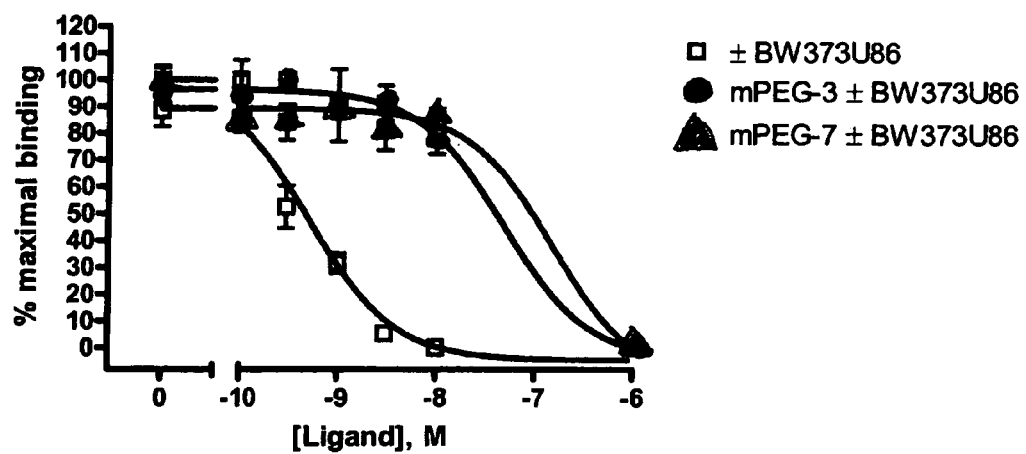
FIGS. 1 and 2 show opioid delta receptor binding assay for BW373U86 and BW373U86-PEG conjugates to CHO-delta clone #16.
Figure 2:
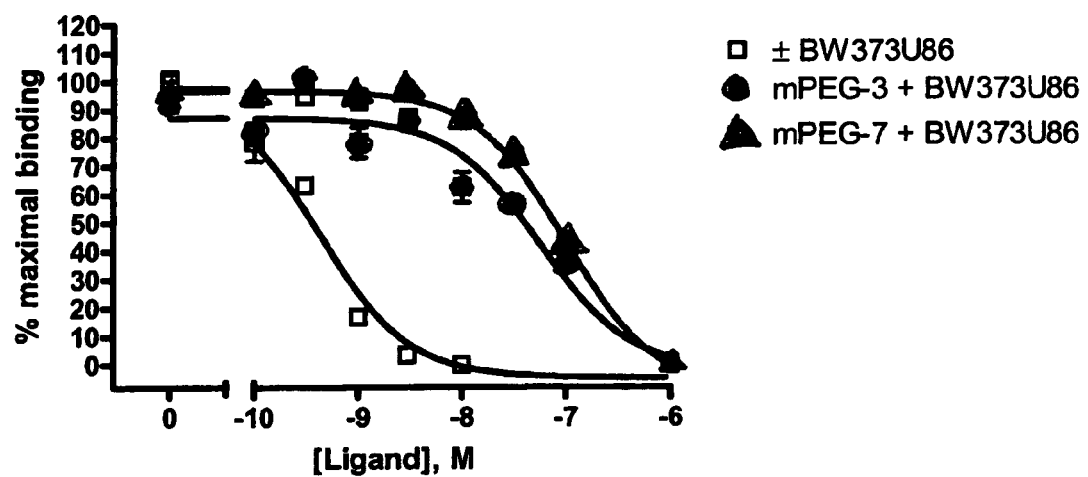

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though, the oligomer may contain distinct end capping moieties or functional groups, e.g., for conjugation. PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from about 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched," in reference to the geometry or overall structure of an oligomer, refers to an oligomer having two or more polymers "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the therapeutic moiety. A composition comprised of monodisperse conjugates may, however, include one or more non-conjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the therapeutic moiety. A composition comprised of bimodal conjugates may, however, include one or more non-conjugate substances such as solvents, reagents, excipients, and so forth.

An "opioid diarylpiperazine" is broadly used herein to refer to an organic, inorganic, or organometallic compound having a molecular weight of less than about 1000 Daltons and having some degree of activity as antihypertensive therapeutic. Antihypertensive activity of a compound may be measured by assays known in the art and also as described herein later.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it ever reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a conjugate of the invention may provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, and t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

Chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding multivalent moiety, arylene). All atoms are understood to have their normal number of valences for bond formation (i.e., 1 for H, 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

"Nil" refers to the absence of a substituent group. Thus, when a substituent is nil, the substituent may be represented in the structure as a chemical bond or hydrogen in the resulting structure.

As indicated above, the present invention is directed to (among other things) a compound comprising an opioid diarylpiperazine residue covalently attached via a stable or degradable linkage to a water-soluble, non-peptidic oligomer.

The "opioid diarylpiperazine residue" is a compound having a structure of an opioid diarylpiperazine compound that is altered by the presence of one or more bonds, which bonds serve to attach (either directly or indirectly) one or more water-soluble, non-peptidic oligomers. Exemplary opioid diarylpiperazines have a structure encompassed by at least one of the structures defined herein as Formula I:

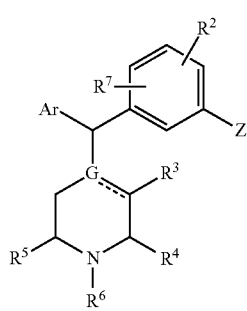

Formula I wherein:
Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined to the compound at a ring carbon atom of the Ar ring;

Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;
sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;
sulfones of the formula $SO_2R^8$ where $R^8$ is the same as above; nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl; carboxamides of the formula $CONR^9R^{10}$ where $R^9$ and $R^{10}$ are the same as above;
sulfonamides of the formula $SO_2NR^9R^{10}$ where $R^9$ and $R^{10}$ are the same as above; and
$CONR^9AB$, where:
A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of hydroxyl, and acyl esters thereof whose acyl moiety is selected from the group consisting of $CH_3CO$, $C_6H_5CO$, $(CH_3)_2NCO$, and $Me_3CCO$;

hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;

$R^1$ is hydrogen, halogen, or $C_1$-$C_4$;

$R^2$ is hydrogen, halogen, or $C_1$-$C_4$;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of hydrogen; $C_1$-$C_6$ alkyl; $C_3$-$C_6$ cycloalkyl; allyl; 2-buten-1-yl; 2-methyl-2-propen-1-yl; 2-chloro-2-propen-1-yl; alkoxyalkyl having $C_1$-$C_4$ alkoxy and $C_1$-$C_4$ alkyl moieties; $C_2$-$C_4$ cyanoalkyl; $C_2$-$C_4$ hydroxyalkyl;

aminocarbonylalkyl having a $C_1$-$C_4$ alkyl moiety; alkylaryl having $C_1$-$C_4$ alkylene and $C_6$-$C_{14}$ aryl moieties; and $R^{12}COR^{13}$, where $R^{12}$ is $C_1$-$C_4$ alkylene, and $R^{13}$ is $C_1$-$C_4$ alkyl or $C_1$-$C_4$ alkoxy; and $R^7$ is hydrogen or fluorine, subject to the proviso that: $R^1$, $R^2$ and $R^7$ may be fluorine only when Z is —OH.

In one or more embodiments of the invention, a compound is provided, the compound comprising an opioid diarylpiperazine residue covalently attached via a stable or degradable linkage to a water-soluble, non-peptidic oligomer, wherein the opioid diarylpiperazine has a structure encompassed by the following formula:

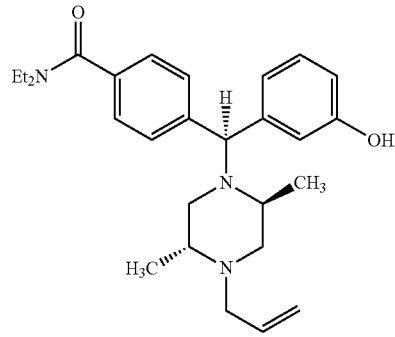

4-((S)-((2S,5R)-4-allyl-2,5-dimethylpiperazin-1-yl)(3-hydroxyphenyl)methyl)-N,N-diethylbenzamide.

In one or more embodiments of the invention, a compound is provided, the compound comprising an opioid diarylpiperazine residue covalently attached via a stable or degradable linkage to a water-soluble, non-peptidic oligomer, wherein the opioid diarylpiperazine has a structure encompassed by the following formula:

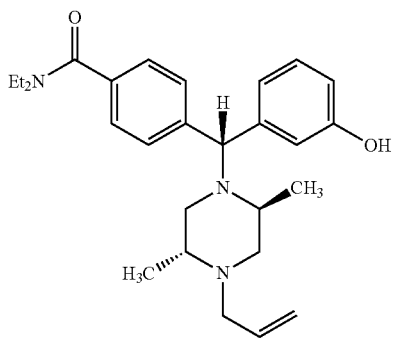

4-((R)-((2S,5R)-4-allyl-2,5-dimethylpiperazin-1-yl)(3-hydroxyphenyl)methyl)-N,N-diethylbenzamide.

In one or more embodiments of the invention, a compound is provided, the compound comprising an opioid diarylpiperazine residue covalently attached via a stable or degradable linkage to a water-soluble, non-peptidic oligomer, wherein the opioid diarylpiperazine has a structure encompassed by the following formula:

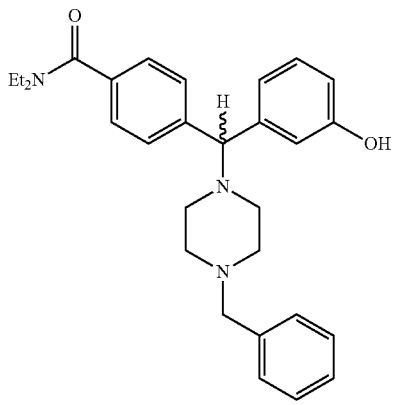

4-((4-benzylpiperazin-1-yl)(3-hydroxyphenyl)methyl)-N,N-diethylbenzamide, and enantiomers and diastereomers thereof.

In one or more embodiments of the invention, a compound is provided, the compound comprising an opioid diarylpiperazine residue covalently attached via a stable or degradable linkage to a water-soluble, non-peptidic oligomer, wherein the opioid diarylpiperazine has a structure encompassed by the following formula:

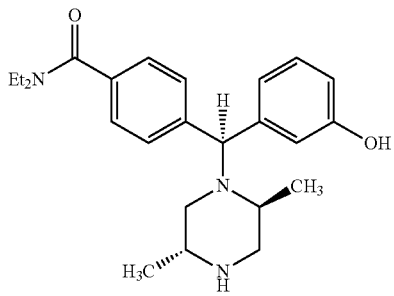

4-((S)-((2S,5R)-2,5-dimethylpiperazin-1-yl)(3-hydroxyphenyl)methyl)-N,N-diethylbenzamide.

In one or more embodiments of the invention, a compound is provided, the compound comprising an opioid diarylpiperazine residue covalently attached via a stable or degradable linkage to a water-soluble, non-peptidic oligomer, wherein the opioid diarylpiperazine has a structure encompassed by the following formula:

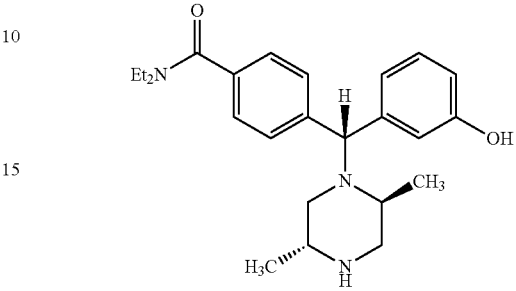

4-((R)-((2S,5R)-2,5-dimethylpiperazin-1-yl)(3-hydroxyphenyl)methyl)-N,N-diethylbenzamide.

In some instances, opioid diarylpiperazines can be obtained from commercial sources. In addition, opioid diarylpiperazines can be obtained through chemical synthesis. Examples of opioid diarylpiperazines as well as synthetic approaches for preparing opioid diarylpiperazines are described in the literature and in, for example, U.S. Pat. No. 5,658,908, and Chang, K. J., et al; J. Pharmacol. Exp. Ther. 267, 852-857 (1993). Each of these (and other) opioid diarylpiperazines can be covalently attached (either directly or through one or more atoms) to a water-soluble, non-peptidic oligomer.

Exemplary compounds of the invention include those having the following structure:

Formula I-C

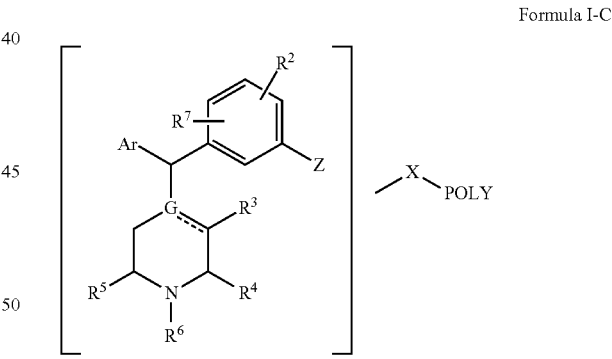

wherein:
Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined at a ring carbon atom (i.e., at a ring carbon atom of Ar);
Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;
sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;
sulfones of the formula $SO_2R^8$ where $R^8$ is the same as above;

nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl;

carboxamides of the formula $CONR^9R^{10}$ where $R^9$ and $R^{10}$ are the same as above;

sulfonamides of the formula $SO_2NR^9R^{10}$ where $R^9$ and $R^{10}$ are the same as above; and $CONR^9AB$, where:

A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of hydroxyl, and acyl esters thereof whose acyl moiety is selected from the group consisting of $CH_3CO$, $C_6H_5CO$, $(CH_3)_2NCO$, and $Me_3CCO$; hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;

$R^1$ is hydrogen, halogen, or $C_1$-$C_4$;

$R^2$ is hydrogen, halogen, or $C_1$-$C_4$;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of hydrogen; $C_1$-$C_6$ alkyl; $C_3$-$C_6$ cycloalkyl; allyl; 2-buten-1-yl; 2-methyl-2-propen-1-yl; 2-chloro-2-propen-1-yl; alkoxyalkyl having $C_1$-$C_4$ alkoxy and $C_1$-$C_4$ alkyl moieties; $C_2$-$C_4$ cyanoalkyl; $C_2$-$C_4$ hydroxyalkyl; aminocarbonylalkyl having a $C_1$-$C_4$ alkyl moiety; alkylaryl having $C_1$-$C_4$ alkylene and $C_6$-$C_{14}$ aryl moieties; and $R^{12}COR^{13}$, where $R^{12}$ is $C_1$-$C_4$ alkylene, and $R^{13}$ is $C_1$-$C_4$ alkyl or $C_1$-$C_4$ alkoxy;

$R^7$ is hydrogen or fluorine, subject to the proviso that: $R^1$, $R^2$ and $R^7$ may be fluorine only when Z is —OH;

X is a spacer moiety and is covalently attached to an atom; and POLY is a water-soluble, non-peptidic oligomer.

Further exemplary compounds of the invention include those having the following structure:

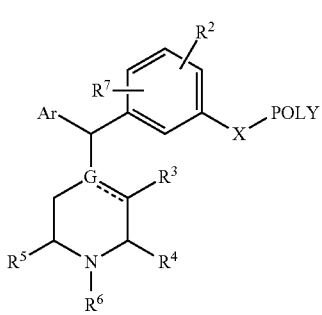

Formula Ia-C wherein:

Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined at a ring carbon atom (i.e., at a ring carbon atom of Ar);

Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;

sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;

sulfones of the formula $SO_2R^8$ where $R^8$ is the same as above;

nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl;

carboxamides of the formula $CONR^9R^{10}$ where $R^9$ and $R^{10}$ are the same as above;

sulfonamides of the formula $SO_2NR^9R^{10}$ where $R^9$ and $R^{10}$ are the same as above; and $CONR^9AB$, where:

A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

G is nitrogen;

$R^1$ is hydrogen, halogen, or $C_1$-$C_4$;

$R^2$ is hydrogen, halogen, or $C_1$-$C_4$;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of hydrogen; $C_1$-$C_6$ alkyl; $C_3$-$C_6$ cycloalkyl; allyl; 2-buten-1-yl; 2-methyl-2-propen-1-yl; 2-chloro-2-propen-1-yl; alkoxyalkyl having $C_1$-$C_4$ alkoxy and $C_1$-$C_4$ alkyl moieties; $C_2$-$C_4$ cyanoalkyl; $C_2$-$C_4$ hydroxyalkyl; aminocarbonylalkyl having a $C_1$-$C_4$ alkyl moiety; alkylaryl having $C_1$-$C_4$ alkylene and $C_6$-$C_{14}$ aryl moieties; and $R^{12}COR^{13}$, where $R^{12}$ is $C_1$-$C_4$ alkylene, and $R^{13}$ is $C_1$-$C_4$ alkyl or $C_1$-$C_4$ alkoxy;

$R^7$ is hydrogen or fluorine;

X is a spacer moiety; and

POLY is a water-soluble, non-peptidic oligomer.

Exemplary compounds of the invention include those having the following structure:

Formula Ib-C

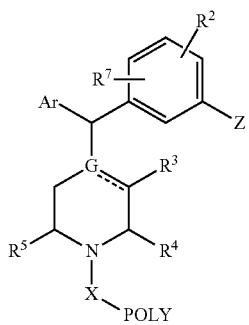

wherein:
Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R_1$, wherein Ar is joined at a ring carbon atom (i.e., at a ring carbon atom of Ar);
Y is selected from the group consisting of hydrogen; halogen; $C_1$-$C_6$ alkyl; $C_1$-$C_6$ haloalkyl; $C_3$-$C_6$ cycloalkyl; $C_1$-$C_6$ alkoxy; $C_3$-$C_6$ cycloalkoxy;
sulfides of the formula $SR^8$ where $R^8$ is $C_1$-$C_6$ alkyl, $C_3$-$C_6$ cycloalkyl, or phenyl; sulfoxides of the formula $SOR^8$ where $R^8$ is the same as above;
sulfones of the formula $SO_2R^8$ where $R^8$ is the same as above; nitrile; $C_1$-$C_6$ acyl; alkoxycarbonylamino (carbamoyl) of the formula $NHCO_2R^8$ where $R^8$ is the same as above; carboxylic acid, or an alkyl ester; aminomethyl of the formula $CH_2NR^9R^{10}$ where $R^9$ and $R^{10}$ may be the same or different, and may be hydrogen, $C_1$-$C_6$ alkyl, $C_2$-$C_6$ hydroxyalkyl, $C_2$-$C_6$ methoxyalkyl, $C_3$-$C_6$ cycloalkyl, or phenyl, or $R^9$ and $R^{10}$ together may form a ring selected from the group consisting of pyrrolidinyl, piperidinyl, and 4-methyl-piperazinyl; carboxamides of the formula $CONR^9R^{10}$ where $R^9$ and $R^{10}$ are the same as above;
sulfonamides of the formula $SO_2NR^9R^{10}$ where $R^9$ and $R^{10}$ are the same as above; and
$CONR^9AB$, where:
A is a divalent ligand having an alkyl or polyether moiety of 6-12 atoms, with the proviso that there are at least two carbon atoms between an oxygen atom and the $NR^9$ group and at least two carbon atoms between two oxygen atoms when present; and
B is a dimer-forming moiety which is joined to a first valence bond of the divalent ligand A, and which is symmetric about the divalent ligand A to the compound moiety joined to the other valence bond of the divalent ligand A;
Z is selected from the group consisting of hydroxyl, and acyl esters thereof whose acyl moiety is selected from the group consisting of $CH_3CO$, $C_6H_5CO$, $(CH_3)_2NCO$, and $Me_3CCO$; hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;
G is nitrogen;
$R^1$ is hydrogen, halogen, or $C_1$-$C_4$;
$R^2$ is hydrogen, halogen, or $C_1$-$C_4$;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;
$R^7$ is hydrogen or fluorine, subject to the proviso that: $R^1$, $R^2$ and $R^7$ may be fluorine only when Z is —OH;
X is a spacer moiety; and
POLY is a water-soluble, non-peptidic oligomer.

Use of discrete oligomers (e.g., from a monodisperse or bimodal composition of oligomers, in contrast to relatively impure compositions) to form oligomer-containing compounds may advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., J. Med. Chem. 2000, 43, 3714-3717; and Kelder, J., et al., Pharm. Res. 1999, 16, 1514-1519.

With respect to the blood-brain barrier, the water-soluble, non-peptidic oligomer-small molecule drug conjugate exhibits a blood-brain barrier crossing rate that is reduced as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate of the invention is at least about 20%.

Assays for determining whether a given compound (regardless of whether the compound includes a water-soluble, non-peptidic oligomer or not) can act as an opioid diarylpiperazine are known and/or may be prepared by one of ordinary skill in the art and are further described infra.

Each of these (and other) diarylpiperazine moieties can be covalently attached (either directly or through one or more atoms) to a water-soluble, non-peptidic oligomer.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300 Daltons.

The small molecule drug used in the invention, if chiral, may be obtained from a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a, phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The opioid diarylpiperazine moiety for coupling to a water-soluble, non-peptidic oligomer possesses a free hydroxyl, carboxyl, thio, amino group, or the like (i.e., "handle") suitable for covalent attachment to the oligomer. In addition, the opioid diarylpiperazine moiety may be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3-(OCH_2CH_2)_n-$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the opioid diarylpiperazine (in contrast to the step-wise addition of one or more monomers to effectively "grow" the oligomer onto the opioid diarylpiperazine), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the opioid diarylpiperazine moiety) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "—" (i.e., a covalent bond, that may be stable or degradable, between the opioid diarylpiperazine residue and the water-soluble, non-peptidic oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, and guanidine. In some instances, a portion or a functional group of the drug compound may be modified or removed altogether to facilitate attachment of the oligomer. In some instances, it is preferred that X is not an amide, i.e., —CONR— or —RNCO—).

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the opioid diarylpiperazine) with a corresponding functional group within the opioid diarylpiperazine. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazolyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O—(CH_2—CH_2—O)_n—(CH_2)_p—C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The termini of the water-soluble, non-peptidic oligomer not bearing a functional group may be capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the opioid diarylpiperazine may not have a functional group suited for conjugation. In this instance, it is possible to modify (or "functionalize") the "original" opioid diarylpiperazine so that it does have a functional group suited for conjugation. For example, if the opioid diarylpiperazine has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule opioid diarylpiperazine bearing a carboxyl group wherein the carboxyl group-bearing small molecule opioid diarylpiperazine is coupled to an amino-terminated oligomeric ethylene glycol, to provide a conjugate having an amide group covalently linking the small molecule opioid diarylpiperazine to the oligomer. This can be performed, for example, by combining the carboxyl group-bearing small molecule opioid diarylpiperazine with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule opioid diarylpiperazine bearing a hydroxyl group wherein the hydroxyl group-bearing small molecule opioid diarylpiperazine is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule opioid diarylpiperazine moiety bearing a hydroxyl group wherein the hydroxyl group-bearing small molecule opioid diarylpiperazine moiety is coupled to an oligomeric ethylene glycol bearing an haloformate group [e.g., $CH_3(OCH_2CH_2)_nOC(O)$-halo, where halo is chloro, bromo, iodo] to result in a carbonate [—O—C(O)—O—] linked small molecule conjugate. This can be performed, for example, by combining an opioid diarylpiperazine moiety and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule opioid diarylpiperazine bearing a ketone group by first reducing the ketone group to form the corresponding hydroxyl group. Thereafter, the small molecule opioid diarylpiperazine now bearing a hydroxyl group can be coupled as described herein.

In still another instance, it is possible to prepare a conjugate of a small molecule opioid diarylpiperazine bearing an amine group. In one approach, the amine group-bearing small molecule opioid diarylpiperazine and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule opioid diarylpiperazine and the carbonyl carbon of the aldehyde-bearing oligomer.

In another approach for preparing a conjugate of a small molecule opioid diarylpiperazine bearing an amine group, a carboxylic acid-bearing oligomer and the amine group-bearing small molecule opioid diarylpiperazine are combined, typically in the presence of a coupling reagent (e.g., DCC). The result is an amide linkage formed between the amine group of the amine group-containing small molecule opioid diarylpiperazine and the carbonyl of the carboxylic acid-bearing oligomer.

While it is believed that the full scope of the conjugates disclosed herein behave as described, an optimally sized oligomer can be identified as follows.

First, an oligomer obtained from a monodisperse or bimodal water soluble oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the opioid diarylpiperazine or the conjugate of an opioid diarylpiperazine and a water-soluble non-peptidic polymer has activity as an opioid diarylpiperazine therapeutic, it is possible to test such a compound. The opioid diarylpiperazine compounds may be tested using in vitro binding studies to receptors using various cell lines expressing these receptors that have become routine in pharmaceutical industry. For example, Befort et al., describe the following assay:

Expression of Wild-type mDOR and Mutant Receptors in COS Cells and Ligand Binding COS-1 cells ($1.5 \times 10^6$ cells/140-mm dish) were transfected with purified plasmids (35 μg/dish) using the DEAE-dextran method. After 72 hours growth in Dulbecco's modified Eagle's medium with 10% fetal calf serum, the cells were harvested and membranes were prepared. For binding experiments, various amounts of membrane proteins of mDOR and mutant receptors, ranging from 20 to 100 μg, were diluted in 50 mM Tris-HCl, pH 7.4, and incubated for 1 hour at 25° C. with opioid ligands in a final volume of 0.5 ml. For saturation experiments, eight concentrations of [$^3$H]diprenorphine ranging from 0.05 to 10 nM (for WT, Y129F, W173A, F218A, Y308F) and eight concentrations of [$^3$H]naltrindole ranging from 0.1 to 12 nM (for WT, Y129A, F222A, W274A) were used. Nonspecific binding was determined in the presence of 2 µM (for WT and F218A), 0.1 mM (for Y129F, W173A, and Y308F), or 0.5 mM (for Y129A, F222A, and W274A) naloxone. For competition studies, membrane preparations were incubated with [$^3$H]diprenorphine (1 nM for WT, Y129F, F218A and 2 nM for W173A and Y308F) or [$^3$H]naltrindole (2 nM for Y129A, F222A, Y308F), in the presence of variable concentrations of opioid competing ligands. When using endogenous peptides as competitors, assays were conducted in the presence of a mixture of protease inhibitors (leupeptin, pepstatin, aprotinin, antipain, and chymostatin, each at 2.5 mg/ml). $K_d$, $K_i$, and $B_{max}$ values were calculated using the EBDA/Ligand program (G. A. McPherson, Biosoft, Cambridge, United Kingdom).

Binding characteristics for various receptors including, but not limited to, delta, kappa, and mu opioid receptors are determined. A representative data set using positive and negative controls is shown below.

Delta Opioid Receptor Binding:

| | |
|---|---|
| Kd (binding affinity) | Forebrain |
| Bmax | 2.1E−9 |
| Ligand | 4.5 fmol/mg tissue (wet weight) |
| Ligand (M) | [3H]Enkephalin, DPDPE |
| Non-Specific | 1E−9 |
| Reference Compound | 1E−6 |
| Method | DPDPE |
| Measurement | Radioactivity |
| Non-specific (M) | DPDPE |

Further, concerning specific receptor ligands, the distinction between delta receptor agonists and antagonists is made by their activity in the electrically stimulated mouse vas deferens assay, which typically has been considered the appropriate diagnostic tissue for the delta receptor. By contrast, mu receptor agonists are generally characterized by their activity in the electrically stimulated guinea pig ileum assay. Thus, conjugates of the present invention and other compounds may suitably be tested in such assays. For example, U.S. Pat. No. 5,658,908 provides following assays:

In vitro bioassays: Vasa deferentia are removed from mice and suspended between platinum electrodes with 0.5 g of tension in organ bath chambers containing a modified Krebs' buffer of the following composition (millimolar): NaCl, 118; KCl, 4.75; CaCl.sub.2, 2.6; KH.sub.2 PO.sub.4, 1.20; NaHCO.sub.3, 24.5; and glucose, 11. The buffer is saturated with 95% $O_2$/5% $CO_2$ and kept at 37° C. Tissues are stimulated at supramaximal voltage with 10 Hz pulse trains for 400 msec; train interval 10 seconds; and 0.5 msec pulse duration. Intact ileums (about 3 cm length) are removed from guinea pig and suspended with 1 g of tension in a bath chamber as described. The modified Krebs' buffer also contained $MgSO_4$ (1.2 mM). The ileums are stimulated with electrical square-wave pulses of 0.1 Hz, 0.5 msec pulse duration at supramaximal voltage. The percentage inhibition of the electrically induced muscle contractions is determined for the compounds at varying cumulative concentrations. The $ED_{50}$ values are extrapolated from curves showing the dose concentration plotted against the response (J. A. H. Lord, A. A. Waterfield, J. Hughes, H. W. Kosterlitz, Nature 267, 495, (1977)).

Inhibition of receptor binding: Rat (Sprague-Dawley) brain membranes are prepared and binding assays are performed at 24° C. for 60 min. as described by Chang, et. al (J. Biol. Chem. 254, 2610 (1979) and Mol. Pharmacol. 16, 91 (1979)) with a filtration method (GF/C filter). Delta receptor binding assays are performed with $^{125}$I-labeled [D-Ala$^2$, D-Leu$^5$] enkephalin (0.24 nM) in the presence of the highly selective mu-agonist [N-MePhe$^3$, D-Pro$^4$] morphiceptin to suppress mu-receptor cross-reactivity. Mu receptor binding assays are performed with $^{125}$I-labeled [D-Ala$^2$, N-MePhe$^4$, Met(O)ol$^5$] enkephalin (0.1 nM). Non-specific binding is determined in the presence of 1 µM of the respective unlabeled ligand. The potency of compounds in inhibiting the binding of $^{125}$I-labeled enkephalin analogs is determined as the concentration which reduced the binding of the labeled compounds by 50 percent ($IC_{50}$).

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by a 300 MHz NMR spectrometer manufactured by Bruker. A list of certain compounds as well as the source of the compounds is provided below.

Example 1

The syntheses of PEG conjugates of BW373U86 and its analogs.

Scheme 1:

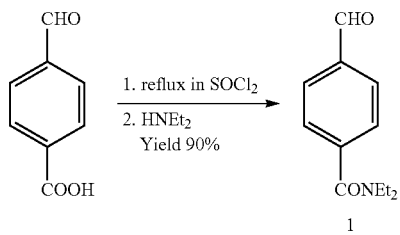

N,N-Diethyl-4-formylbenzamide (1)

4-Carboxybenzaldehyde (1.07 g, 7.13 mmol) was added into $SOCl_2$ (5 ml). The mixture was refluxed for 6 hours until the solid was totally dissolved in solution. Then $SOCl_2$ was evaporated under reduced pressure. Toluene (10 ml) was added to the residue and then removed under reduced pressure. The resulting residue was dissolved in anhydrous DCM (10 ml). $Et_2NH$ (20 mmol, 2.07 ml) was added dropwise. The solution was stirred at room temperature overnight. The solvent was removed under reduced pressure and the resulting residue was subjected to flash chromatography (EtOAc/Hexanes=30%-50%) to give compound (I) (1.32 g, 6.44 mmol, yield 90%). $^1$H NMR ($CDCl_3$) δ 10.06 (s, 1H), 7.95 (d, 2H), 7.55 (d, 2H), 3.58 (quart, 2H), 3.23 (quart, 2H), 1.28 (t, 3H), 1.13 (t, 3H).

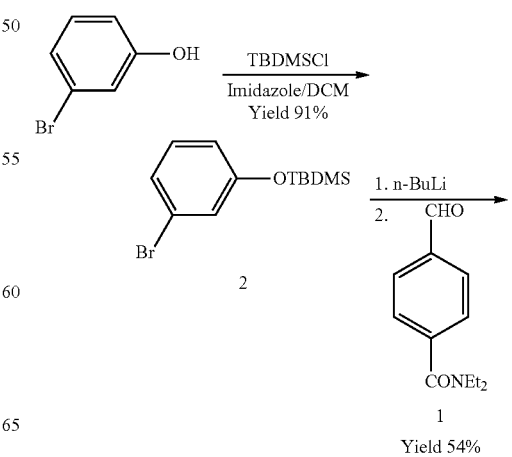

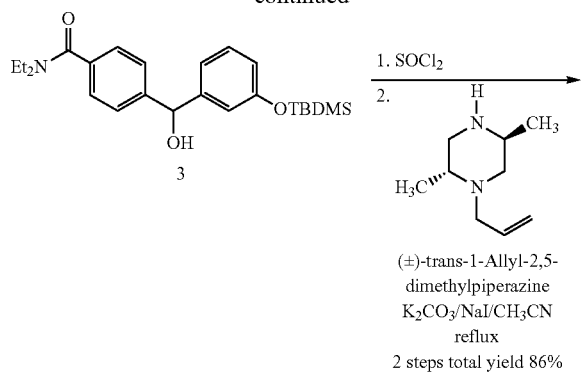

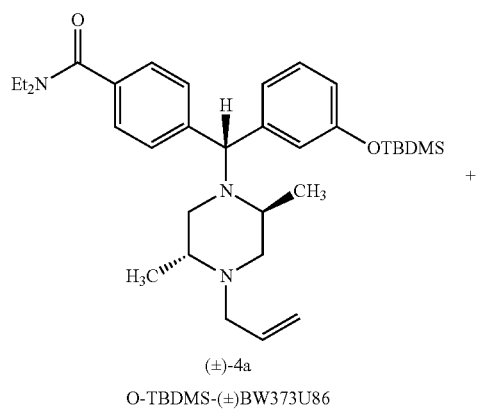

O-TBDMS-(±)BW373U86

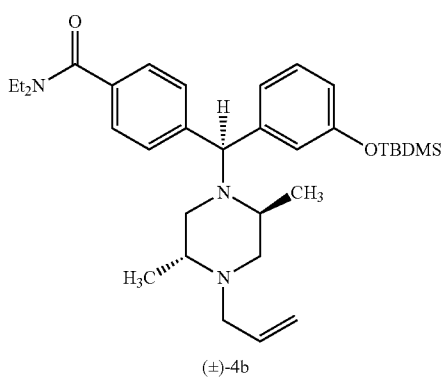

3-Bromophenyl tert-butyldimethylsilyl ether (2)

3-Bromophenol (6 mmol, 1.04 g), imidazole (10 mmol, 0.68 g) and TBDMSCl (6.6 mmol, 0.99 g) were dissolved in DCM (20 ml). The solution was allowed to stir at room temperature overnight. The solid generated during the reaction was filtered off and the solvent removed under reduced pressure. The resulting residue was subjected to flash chromatography (EtOAc/Hexanes=3%~15%) giving compound 2 (1.56 g, 5.44 mmol, yield 91%). $^1$H NMR (CDCl$_3$): δ 7.11-7.08 (m, 2H), 7.03-7.02 (m, 1H), 6.80-6.77 (m, 1H), 0.99 (s, 9H), 0.31 (s, 6H).

N,N-Diethyl-4-[hydroxy-(3-O-TBDMS-phenyl)-methyl]benzamide (3)

Compound 2 (1.55 g, 5.42 mmol) was dissolved in anhydrous THF (30 ml). At −78° C., n-BuLi solution (3.44 ml, 5.5 mmol, 1.6 M in Hexanes solution) was added dropwise. After 30 minutes, a solution of compound 1 (1.13 g, 5.50 mmol) in THF (8 ml) was added dropwise with stirring. The reaction solution was allowed to warm up to room temperature in a period of 3 hrs. Then a saturated NH$_4$Cl solution (5 ml) was added to quench the reaction. The solution was extracted with DCM (20 ml×3). The organic phases were combined, dried over Na$_2$SO$_4$, filtered, and the solvent removed under reduced pressure. The resulting residue was subjected to flash chromatography (EtOAc/Hexanes=12%~60%) to give compound 3 (1.23 g, 2.97 mmol, yield 54%). $^1$H NMR (CDCl$_3$): δ 7.33 (d, 2H), 7.23 (d, 2H), 7.15-7.12 (m, 1H), 6.94-6.91 (m, 1H), 6.84-6.83 (m, 1H), 6.73-6.70 (m, 1H), 5.69 (d, 1H), 3.73 (d, 1H), 3.48 (m, 2H), 3.22 (m, 2H), 1.19 (m, 3H), 1.08 (m, 3H), 0.97 (s, 9H), 0.15 (s, 6H).

(±)-4-[(αR)-α-((2S,5R)-4-Allyl-2,5-dimethyl-1-piperazinyl)-3-O-TBDMS-benzyl]-N,N-diethylbenzamid [(±)-4-a]

Compound 3 (800 mg, 1.94 mmol) was dissolved in DCM (20 ml). SOCl$_2$ (3 mmol, 0.22 ml) was added to the solution at room temperature and continued to stir at room temperature for 1 hour once addition was complete. After 1 hour, the solvent was removed under reduced pressure and toluene (10 ml) was added. The toluene was subsequently removed under reduced pressure and the resulting residue, without further purification, was mixed with (±)-trans-1-allyl-2,5-dimethylpiperazine (3.0 mmol, 459 mg), K$_2$CO$_3$ (6 mmol, 828 mg), NaI (3 mmol, 450 mg) in anhydrous acetonitrile (20 ml). The reaction solution was stirred and refluxed overnight. The solid was filtered off and the solvent was removed under reduced pressure. The resulting residue was subjected to flash chromatography (EtOAc/Hexanes=20%~80%) giving (±)-4-a (450 mg, 0.82 mmol, yield 42%) as the first spot to elute and (±)-4-b (460 mg, 0.84 mmol, yield 43%) as the second spot to elute.

Compound (±)-4-a: $^1$H NMR (CDCl$_3$): δ 7.47 (d, 2H), 7.30 (d, 2H), 7.20-7.15 (m, 1H), 6.80-6.74 (m, 2H), 6.61 (s, 1H), 5.89-5.80 (m, 1H), 5.20-5.11 (m, 3H), 3.54-3.44 (m, 2H), 3.38-3.32 (m, 3H), 2.88-2.77 (m, 2H), 2.60-2.55 (m, 2H), 2.55-2.42 (m, 1H), 2.16-2.09 (m, 1H), 1.89-1.86 (m, 1H), 1.26-1.12 (m, 6H), 1.20 (d, 3H), 0.99 (d, 3H), 0.96 (s, 9H), 0.16 (s, 6H).

Compound (±)-4-b: $^1$H NMR (CDCl$_3$): δ 7.34 (d, 2H), 7.26 (d, 2H), 7.11 (t, 1H), 7.01 (s, 1H), 6.91-6.89 (m, 1H), 6.72-6.69 (m, 1H), 5.87-5.81 (m, 1H), 5.20-5.12 (m, 3H), 3.54-3.44 (m, 2H), 3.38-3.32 (m, 3H), 2.89-2.78 (m, 2H), 2.69-2.49 (m, 3H), 2.16-2.09 (m, 1H), 1.90-1.89 (m, 1H), 1.26-1.17 (m, 6H), 1.19 (d, 3H), 0.99 (d, 3H), 0.96 (s, 9H), 0.16 (s, 6H).

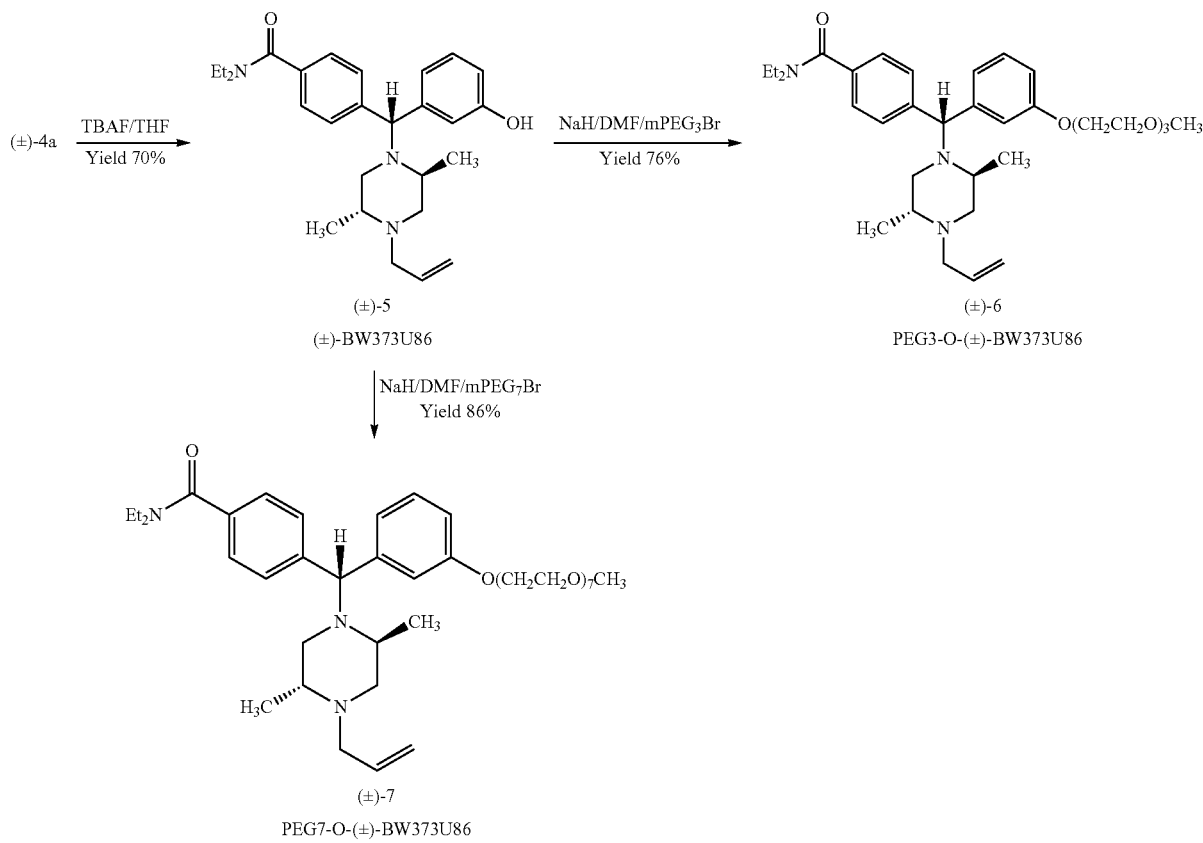

(±)-4-[(αR)-α-((2S,5R)-4-Allyl-2,5-dimethyl-1-piperazinyl)-3-hydroxbenzyl]-N,N-diethylbenzamide [(±)-5)]

Compound (±)-4-a (360 mg, 0.66 mmol) was dissolved in THF (15 ml) and Bu₄NF (1.0 mmol, 1.0 ml, 1.0 M solution in THF) was added to the solution with stirring. The reaction solution was stirred at room temperature for 1.5 hours. The solvent was removed under reduced pressure and the resulting residue was subjected to flash chromatography (MeOH/DCM=2%~5%) to give compound (±)-5 (198 mg, 0.46 mmol, yield 70%). $^1$H NMR (CDCl$_3$): δ 7.45 (d, 2H), 7.39 (d, 2H), 7.10-7.05 (m, 1H), 6.60-6.55 (m, 3H), 5.95-5.84 (m, 1H), 5.25-5.17 (m, 3H), 3.55-3.31 (m, 5H), 2.94-2.85 (m, 2H), 2.66-2.50 (m, 3H), 2.18 (t, 1H), 1.95 (t, 1H), 1.24-0.93 (m, 7H), 1.17 (d, 3H), 1.01 (d, 3H).

(±)-4-[(αR)-α-((2S,5R)-4-Allyl-2,5-dimethyl-1-piperazinyl)-3-O-methoxy(triethylene glycol)benzyl]-N,N-diethylbenzamid [(±)-6]

Compound (±)-5 (100 mg, 0.23 mmol) was dissolved in anhydrous DMF (5 ml) and NaH (20 mg, 60% in mineral oil, 0.5 mmol) was added to the solution at room temperature with stirring. The solution continued to stir at room temperature for 10 minutes at which point, methoxy tri(ethylene glycol) bromide (100 mg, 0.44 mmol) was added. The resulting reaction solution was stirred at room temperature for 2 hours. Sat. NH₄Cl solution (1 ml) was added to the solution and the solvent removed under reduced pressure. The resulting residue was subjected to flash chromatography (MeOH/DCM=2%~6%) to give compound (±)-6 (102 mg, 0.18 mmol, yield 76%). $^1$H NMR (CDCl$_3$): δ 7.45 (d, 2H), 7.28 (d, 2H), 7.21 (t, 1H), 6.82-6.73 (m, 3H), 5.86-5.83 (m, 1H), 5.19-5.11 (m, 3H), 4.06 (t, 2H), 3.84 (t, 2H), 3.73-3.63 (m, 6H), 3.55-3.52 (m, 4H), 3.36 (s, 3H), 3.35-3.31 (m, 3H), 2.80-2.62 (m, 2H), 2.60-2.56 (m, 2H), 2.50-2.45 (m, 1H), 2.12 (t, 1H), 1.89 (t, 1H), 1.22-1.02 (m, 6H), 1.18 (d, 3H), 1.00 (d, 3H). LC/MS 582 [M+H]⁺, 604 [M+Na]⁺.

(±)-4-[(αR)-α-((2S,5R)-4-Allyl-2,5-dimethyl-1-piperazinyl)-3-O-methoxy(heptaethylene glycol)benzyl]-N,N-diethylbenzamid [(±)-7]

Compound (±)-5 (85 mg, 0.20 mmol) was dissolved in anhydrous DMF (5 ml) and NaH (16 mg, 60% in mineral oil, 0.4 mmol) was added to the solution at room temperature with stirring. The solution continued to stir at room temperature for 10 minutes at which point, methoxy hepta(ethylene glycol) bromide (121 mg, 0.30 mmol) was added. The resulting reaction solution was stirred at room temperature for 2 hours. Sat. NH₄Cl solution (1 ml) was added to the solution and the solvent removed under reduced pressure. The resulting residue was subjected to flash chromatography (MeOH/DCM=2%~6%) to give compound (±)-7 (130 mg, 0.17 mmol, yield 86%). $^1$H NMR (CDCl$_3$): δ 7.42 (d, 2H), 7.24 (d, 2H), 7.19 (t, 1H), 6.80-6.71 (m, 3H), 5.85-5.80 (m, 1H), 5.19-5.11 (m, 3H), 4.05 (t, 2H), 3.81 (t, 2H), 3.69-3.59 (m, 22H), 3.52-3.49 (m, 4H), 3.34 (s, 3H), 3.35-3.32 (m, 3H), 2.82-2.75 (m, 2H), 2.61-2.53 (m, 3H), 2.10 (t, 1H), 1.90 (t, 1H), 1.22-1.01 (m, 6H), 1.14 (d, 3H), 0.99 (d, 3H). LC/MS 758 [M+H]$^+$, 780 [M+Na]$^+$.

Scheme 2:

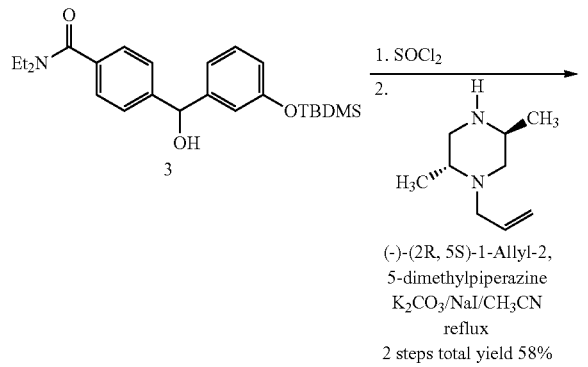

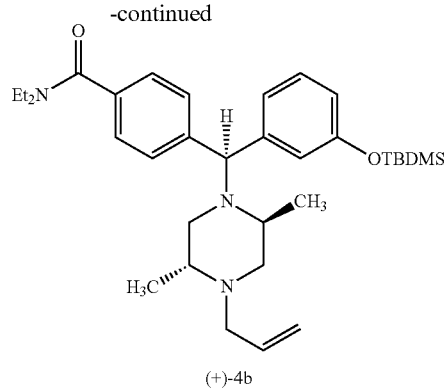

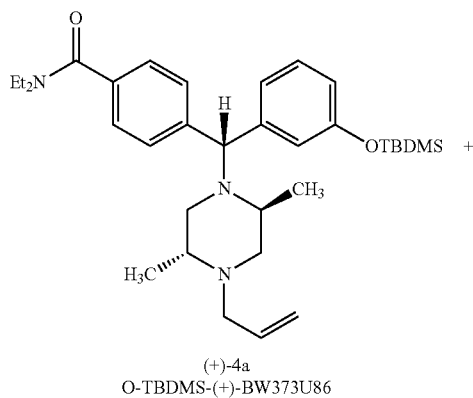

(+)-4-[(αR)-α-((2S,5R)-4-Allyl-2,5-dimethyl-1-piperazinyl)-3-O-TBDMS-benzyl]-N,N-diethylbenzamid [(+)-4-a]

Compound 3 (1.10 g, 2.66 mmol) was dissolved in DCM (20 ml) and SOCl$_2$ (4 mmol, 0.3 ml) was added to the solution at room temperature and continued to stir at room temperature for 1 hour once addition was complete. After 1 hour, the solvent was removed under reduced pressure and toluene (10 ml) was added. The toluene was subsequently removed under reduced pressure and the resulting residue, without further purification, was mixed with (−)-(2R,5S)-1-allyl-2,5-dimethylpiperazine (2.8 mmol, 428 mg), K$_2$CO$_3$ (6 mmol, 828 mg), NaI (3 mmol, 450 mg) in anhydrous acetonitrile (25 ml). The reaction solution was stirred and refluxed overnight. The solid was filtered off and the solvent removed under reduced pressure. The resulting residue was subjected to flash chromatography (EtOAc/Hexanes=20%~80%) giving (+)-4-a (390 mg, 0.73 mmol, yield 27%) as the first spot to elute and (+)-4-b (440 mg, 0.84 mmol, yield 31%) as the second spot to elute.

Compound (+)-4-a: $^1$H NMR (CDCl$_3$): δ 7.47 (d, 2H), 7.30 (d, 2H), 7.20-7.15 (m, 1H), 6.80-6.74 (m, 2H), 6.61 (s, 1H), 5.89-5.80 (m, 1H), 5.20-5.11 (m, 3H), 3.54-3.44 (m, 2H), 3.38-3.32 (m, 3H), 2.88-2.77 (m, 2H), 2.60-2.55 (m, 2H), 2.55-2.42 (m, 1H), 2.16-2.09 (m, 1H), 1.89-1.86 (m, 1H), 1.26-1.12 (m, 6H), 1.20 (d, 3H), 0.99 (d, 3H), 0.96 (s, 9H), 0.16 (s, 6H).

Compound (+)-4-b: $^1$H NMR (CDCl$_3$): δ 7.34 (d, 2H), 7.26 (d, 2H), 7.11 (t, 1H), 7.01 (s, 1H), 6.91-6.89 (m, 1H), 6.72-6.69 (m, 1H), 5.87-5.81 (m, 1H), 5.20-5.12 (m, 3H), 3.54-3.44 (m, 2H), 3.38-3.32 (m, 3H), 2.89-2.78 (m, 2H), 2.69-2.49 (m, 3H), 2.16-2.09 (m, 1H), 1.90-1.89 (m, 1H), 1.26-1.17 (m, 6H), 1.19 (d, 3H), 0.99 (d, 3H), 0.96 (s, 9H), 0.16 (s, 6H).

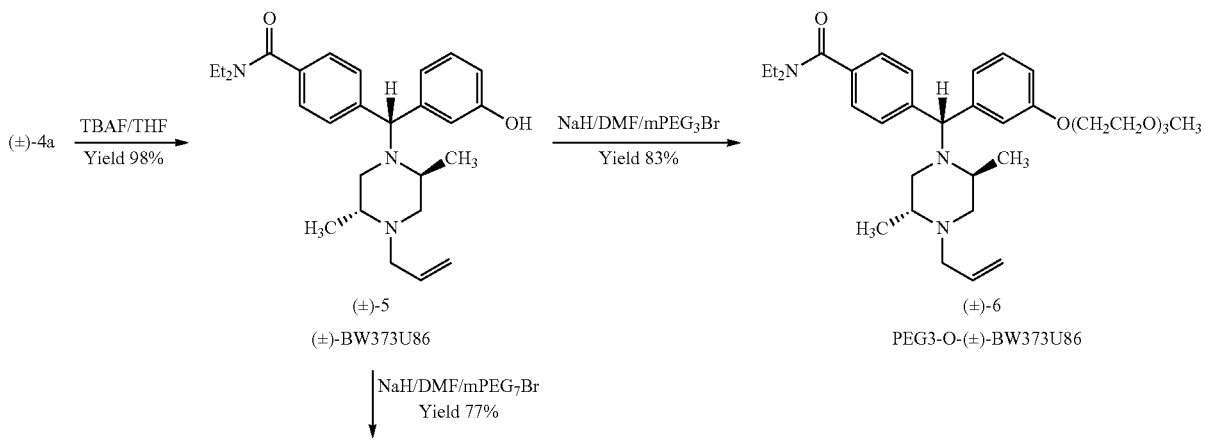

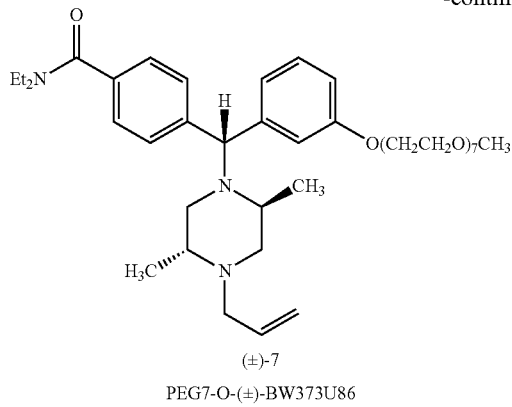

(±)-7
PEG7-O-(±)-BW373U86

(+)-4-[(αR)-α-((2S,5R)-4-Allyl-2,5-dimethyl-1-piperazinyl)-3-hydroxybenzyl]-N,N-diethylbenzamide [(+)-5)]

Compound (+)-4-a (390 mg, 0.73 mmol) was dissolved in THF (20 ml) and Bu$_4$NF (1.1 mmol, 1.1 ml, 1.0 M solution in THF) was added to the solution with stirring. The reaction solution was allowed to stir at room temperature for 1 hour. The solvent was removed under reduced pressure. The resulting residue was subjected to flash chromatography (MeOH/DCM=2%~5%) to give compound (+)-5 (310 mg, 0.71 mmol, yield 98%). $^1$H NMR (CDCl$_3$): δ 7.45 (d, 2H), 7.39 (d, 2H), 7.10-7.05 (m, 1H), 6.60-6.55 (m, 3H), 5.95-5.84 (m, 1H), 5.25-5.17 (m, 3H), 3.55-3.31 (m, 5H), 2.94-2.85 (m, 2H), 2.66-2.50 (m, 3H), 2.18 (t, 1H), 1.95 (t, 1H), 1.24-0.93 (m, 7H), 1.17 (d, 3H), 1.01 (d, 3H).

(+)-4-[(αR)-α-((2S,5R)-4-Allyl-2,5-dimethyl-1-piperazinyl)-3-O-methoxy(triethylene glycopbenzyl]-N,N-diethylbenzamid [(+)-6]

Compound (+)-5 (110 mg, 0.25 mmol) was dissolved in anhydrous DMF (5 ml) and NaH (20 mg, 60% in mineral oil, 0.5 mmol) was added to the solution at room temperature with stirring. The solution continued to stir at room temperature for 10 minutes at which point, methoxy tri(ethylene glycol) bromide (100 mg, 0.44 mmol) was added. The resulting reaction solution was stirred at room temperature for 2 hours. Sat. NH$_4$Cl solution (1 ml) was added to the solution and the solvent removed under reduced pressure. The resulting residue was subjected to flash chromatography (MeOH/DCM=2%~6%) to give compound (+)-6 (120 mg, 0.21 mmol, yield 83%). $^1$H NMR (CDCl$_3$): δ 7.45 (d, 2H), 7.28 (d, 2H), 7.21 (t, 1H), 6.82-6.73 (m, 3H), 5.86-5.83 (m, 1H), 5.19-5.11 (m, 3H), 4.06 (t, 2H), 3.84 (t, 2H), 3.73-3.63 (m, 6H), 3.55-3.52 (m, 4H), 3.36 (s, 3H), 3.35-3.31 (m, 3H), 2.80-2.62 (m, 2H), 2.60-2.56 (m, 2H), 2.50-2.45 (m, 1H), 2.12 (t, 1H), 1.89 (t, 1H), 1.22-1.02 (m, 6H), 1.18 (d, 3H), 1.00 (d, 3H). LC/MS 582 [M+H]$^+$, 604 [M+Na]$^+$.

(±)-4-[(αR)-α-((2S,5R)-4-Allyl-2,5-dimethyl-1-piperazinyl)-3-O-methoxy(heptaethylene glycol)benzyl]-N,N-diethylbenzamid [(+)-7]

Compound (+)-5 (108 mg, 0.25 mmol) was dissolved in anhydrous DMF (5 ml) and NaH (20 mg, 60% in mineral oil, 0.5 mmol) was added to the solution at room temperature with stirring. The solution continued to stir at room temperature for 10 minutes, at which point, methoxy hepta(ethylene glycol) bromide (121 mg, 0.30 mmol) was added. The resulting reaction solution was stirred at room temperature for 2 hours. Sat. NH$_4$Cl solution (1 ml) was added to the solution and the solvent removed under reduced pressure. The resulting residue was subjected to flash chromatography (MeOH/DCM=2%~6%) to give compound (+)-7 (145 mg, 0.19 mmol, yield 77%). $^1$H NMR (CDCl$_3$): δ 7.42 (d, 2H), 7.24 (d, 2H), 7.19 (t, 1H), 6.80-6.71 (m, 3H), 5.85-5.80 (m, 1H), 5.19-5.11 (m, 3H), 4.05 (t, 2H), 3.81 (t, 2H), 3.69-3.59 (m, 22H), 3.52-3.49 (m, 4H), 3.34 (s, 3H), 3.35-3.32 (m, 3H), 2.82-2.75 (m, 2H), 2.61-2.53 (m, 3H), 2.10 (t, 1H), 1.90 (t, 1H), 1.22-1.01 (m, 6H), 1.14 (d, 3H), 0.99 (d, 3H). LC/MS 758 [M+H]$^+$, 780 [M+Na]$^+$.

Scheme 3:

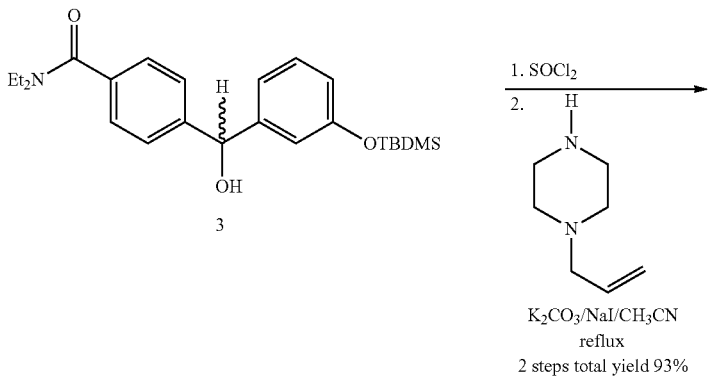

K$_2$CO$_3$/NaI/CH$_3$CN
reflux
2 steps total yield 93%

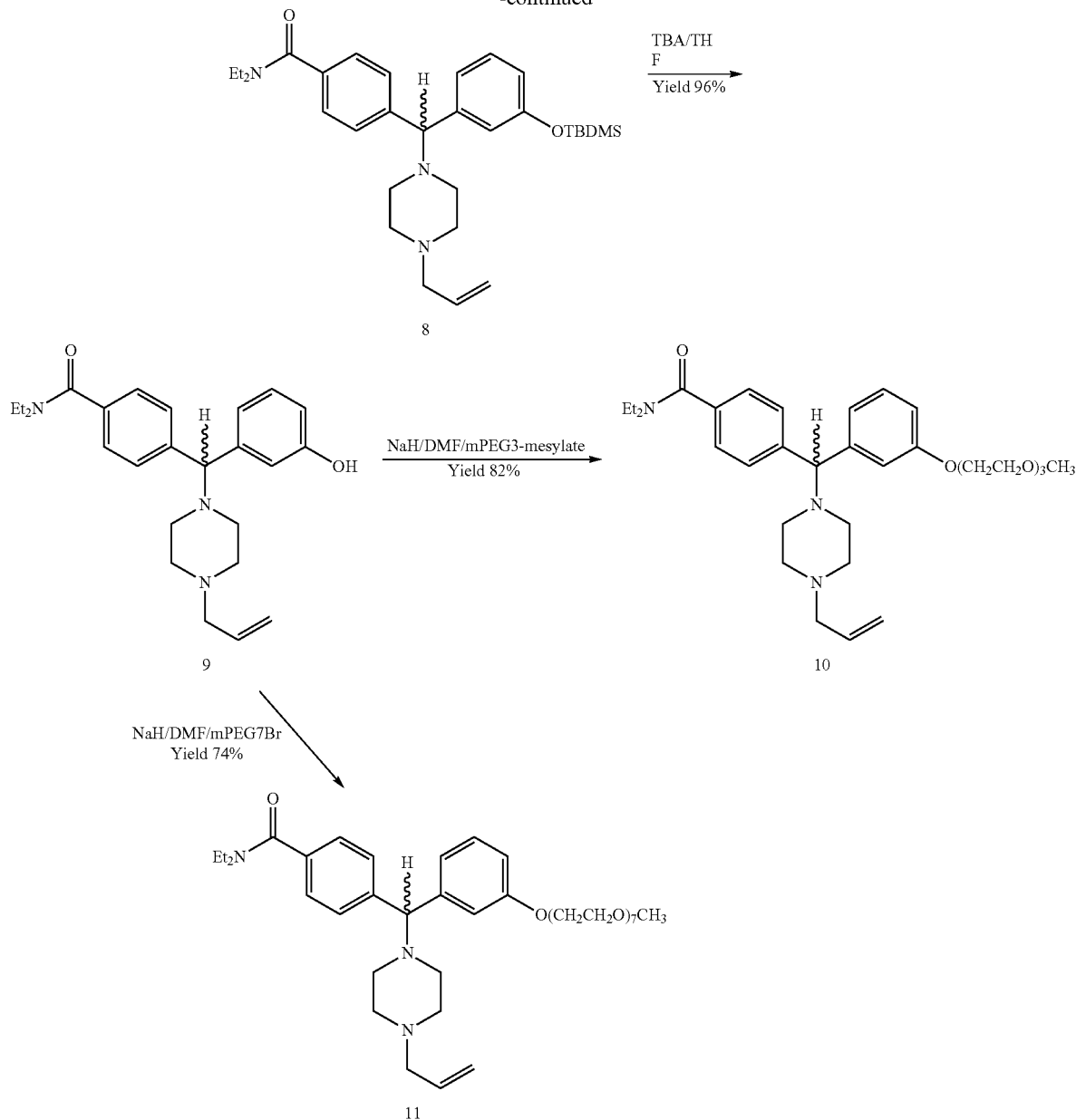

4-[(4-Allyl-1-piperazinyl)-3-O-TBDMS-benzyl]-N,N-diethylbenzamide (8)

Compound 3 (480 mg, 1.16 mmol) was dissolved in DCM (20 ml) and SOCl$_2$ (2.66 mmol, 0.20 ml) was added to the solution at room temperature with stirring. The solution continued to stir at room temperature for 3 hours. Then the solvent was removed under reduced pressure and toluene (10 ml) was added to the resulting residue. The toluene was subsequently removed under reduced pressure and the resulting residue, without further purification, was mixed with 1-allylpiperazine (1.5 mmol, 189 mg), K$_2$CO$_3$ (3 mmol, 414 mg), NaI (1.5 mmol, 225 mg) in anhydrous acetonitrile (20 ml). The reaction solution was stirred and refluxed overnight. The solid was filtered off and the solvent removed under reduced pressure. The resulting residue was subjected to flash chromatography (MeOH/DCM=2%~7%) to give compound 8 (560 mg, 1.07 mmol, yield 93%). $^1$H NMR (CDCl$_3$): δ 7.43 (d, 2H), 7.27 (d, 2H), 7.10 (t, 1H), 6.96-6.91 (m, 2H), 6.67-6.64 (m, 1H), 5.89-5.80 (m, 1H), 5.19-5.10 (m, 3H), 4.17 (s, 1H), 3.54-3.44 (m, 2H), 3.38-3.34 (m, 2H), 2.99 (d, 2H), 2.60-2.40 (m, 7H), 1.26-0.99 (m, 6H), 0.96 (s, 9H), 0.15 (s, 6H).

4-[(4-Allyl-1-piperazinyl)-3-hydroxbenzyl]-N,N-diethylbenzamid (9)

Compound 8 (560 mg, 1.07 mmol) was dissolved in THF (20 ml) and Bu$_4$NF (1.5 mmol, 1.5 ml, 1.0 M solution in THF) was added to the solution with stirring. The reaction solution continued to stir at room temperature for 2.5 hours. The solvent was removed under reduced pressure and the resulting residue was subjected to flash chromatography (MeOH/DCM=2%~10%) to give compound 9 (420 mg, 1.03 mmol, yield 96%). NMR (CDCl$_3$): δ 7.42 (d, 2H), 7.30 (d, 2H), 7.13 (t, 1H), 6.96-6.86 (m, 2H), 6.67-6.64 (m, 1H), 5.92-5.83 (m, 2H), 5.23-5.15 (m, 2H), 4.16 (s, 1H), 3.55-3.45 (m, 2H), 3.36-3.22 (m, 2H), 3.04 (d, 2H), 2.60-2.32 (m, 7H), 1.32-1.03 (m, 6H).

4-[(4-Allyl-1-piperazinyl)-3-O-methoxy(triethyleneglycol)benzyl]-N,N-diethylbenzamid (10)

Compound 9 (84 mg, 0.21 mmol) was dissolved in anhydrous DMF (5 ml) and NaH (16 mg, 60% in mineral oil, 0.4 mmol) was added to the solution at room temperature with stirring. The reaction solution continued to stir at room temperature for 10 minutes at which point, methoxy tri(ethylene glycol) mesylate (96.8 mg, 0.40 mmol) was added. The reaction solution was stirred at room temperature for 24 hours. Sat. NH$_4$Cl solution (1 ml) was added to the solution. The solvent was removed under reduced pressure and the resulting residue was subjected to flash chromatography (MeOH/DCM=2%~11%) giving compound 10 (95 mg, 0.17 mmol, yield 82%) $^1$H NMR (CDCl$_3$): δ 7.42 (d, 2H), 7.27 (d, 2H), 7.16 (t, 1H), 6.99-6.93 (m, 2H), 6.74-6.70 (m, 1H), 5.86-5.81 (m, 1H), 5.20-5.11 (m, 2H), 4.18 (s, 1H), 4.16 (t, 2H), 3.84 (t, 2H), 3.73-3.63 (m, 6H), 3.55-3.50 (m, 3H), 3.37 (s, 3H), 3.25-3.20 (m, 1H), 3.01 (d, 2H), 2.62-2.30 (m, 8H), 1.19-1.00 (m, 6H). LC/MS 554 [M+H]$^+$, 576 [M+Na]$^+$.

4-[(4-Allyl-1-piperazinyl)-3-O-[methoxy(heptaethylene glycol)benzyl]-N,N-diethylbenzamide (11)

Compound 9 (190 mg, 0.47 mmol) was dissolved in anhydrous DMF (5 ml) and NaH (40 mg, 60% in mineral oil, 1.0 mmol) was added to the solution at room temperature with stirring. The reaction solution continued to stir at room temperature for 10 minutes at which point, methoxy hepta(ethylene glycol) bromide (242 mg, 0.60 mmol) was added. The reaction solution was stirred at room temperature for 3.5 hours. Sat. NH$_4$Cl solution (2 ml) was added to the solution. The solvent was removed under reduced pressure and the resulting residue was subjected to flash chromatography (MeOH/DCM=2%~10%) giving compound 11 (255 mg, 0.35 mmol, yield 74%). $^1$H NMR (CDCl$_3$): δ 7.41 (d, 2H), 7.26 (d, 2H), 7.15 (t, 1H), 6.98-6.95 (m, 2H), 6.73-6.70 (m, 1H), 5.86-5.80 (m, 1H), 5.20-5.11 (m, 2H), 4.18 (s, 1H), 4.08 (t, 2H), 3.83 (t, 2H), 3.71-3.62 (m, 22H), 3.53-3.51 (m, 3H), 3.36 (s, 3H), 3.20-3.15 (m, 1H), 3.02 (d, 2H), 2.66-2.30 (m, 8H), 1.19-1.05 (m, 6H). LC/MS 730 [M+H]$^+$, 752 [M+Na]$^+$.

Scheme 4:

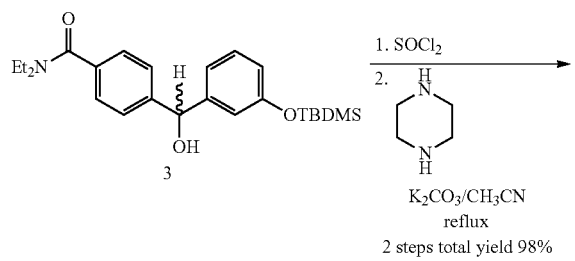

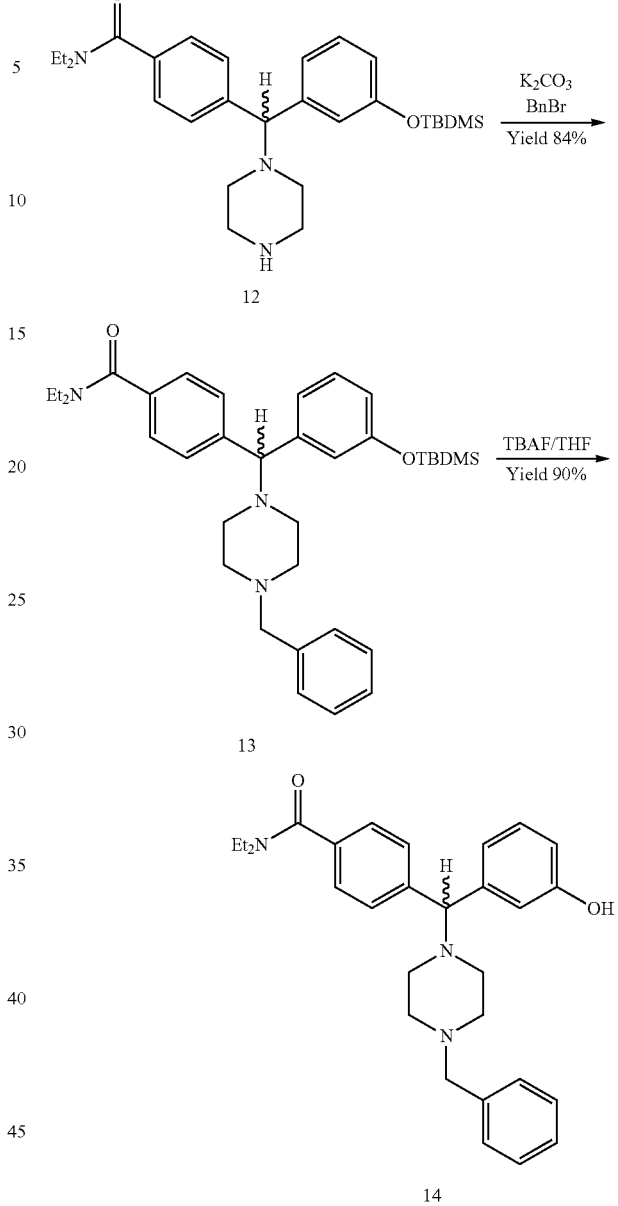

4-[(1-piperazinyl)-3-O-TBDMS-benzyl]-N,N-diethylbenzamid (12)

Compound 3 (190 mg, 0.46 mmol) was dissolved in DCM (10 ml) and SOCl$_2$ (1.33 mmol, 0.10 ml) was added to the solution at room temperature with stirring. The solution continued to stir at room temperature for 3 hours. Then the solvent was removed under reduced pressure and toluene (10 ml) was added to the resulting residue. The toluene was subsequently removed under reduced pressure and the resulting residue, without further purification, was mixed with piperazine (1.38 mmol, 119 mg), K$_2$CO$_3$ (2.3 mmol, 317 mg) in anhydrous acetonitrile (20 ml). The reaction solution was stirred and refluxed for 2 hours. The solvent was removed under reduced pressure. The residue was dissolved in EtOAc (20 ml) which was washed with H$_2$O (20 ml×3). The organic phases were combined, dried over Na$_2$SO$_4$, filtered and the solvent removed under reduced pressure to give compound 12 (220 mg, 0.45 mmol, yield 98%). $^1$H NMR (CDCl$_3$): δ 7.43 (d, 2H), 7.29 (d, 2H), 7.12 (t, 1H), 6.97-6.93 (m, 2H), 6.59-6.65 (m, 1H), 4.17 (s, 1H), 3.54-3.44 (m, 2H), 3.38-3.24 (m, 2H), 2.89-2.86 (d, 4H), 2.40-2.30 (m, 4H), 1.86-1.66 (m, 1H), 1.26-1.10 (m, 6H), 0.96 (s, 9H), 0.15 (s, 6H).

4-[(4-Benzyl-1-piperazinyl)-3-O-TBDMS-benzyl]-N,N-diethylbenzamid (13)

Compound 12 (220 mg, 0.46 mmol) was mixed with benzyl bromide (0.50 mmol, 0.06 ml), K$_2$CO$_3$ (1.0 mmol, 138 mg) in anhydrous acetonitrile (10 ml). The reaction solution was stirred at 50° C. for 30 minutes. The solid was filtered off and the solvent was removed under reduced pressure. The resulting residue was subjected to flash chromatography (EtOAc/Hexanes=20%~70%) to give compound 13 (220 mg, 0.39 mmol, 84%). $^1$H NMR (CDCl$_3$): δ 7.44 (d, 2H), 7.31-7.28 (m, 7H), 7.12 (t, 1H), 6.98-6.94 (m, 2H), 6.70-6.67 (m, 1H), 4.20 (s, 1H), 3.58-3.48 (m, 4H), 3.30-3.20 (m, 2H), 2.60-2.45 (m, 8H), 1.26-1.10 (m, 6H), 0.99 (s, 9H), 0.18 (s, 6H).

4-[(4-Benzyl-1-piperazinyl)-3-hydroxbenzyl]-N,N-diethylbenzamid (14)

Compound 13 (220 mg, 0.39 mmol) was dissolved in THF (20 ml) and Bu$_4$NF (0.70 mmol, 0.7 ml, 1.0 M solution in THF) was added to the solution with stirring. The reaction solution continued to stir at room temperature for 1.5 hours and the solvent was removed under reduced pressure. The resulting residue was subjected to flash chromatography (MeOH/DCM=2%~8%) to give compound 14 (160 mg, 0.35 mmol, yield 90%). $^1$H NMR (CDCl$_3$): δ 7.38-7.23 (m, 9H), 7.03 (t, 1H), 6.87-6.82 (m, 2H), 6.57-6.55 (m, 1H), 4.06 (s, 1H), 3.58-3.50 (m, 4H), 3.30-3.22 (m, 2H), 2.55-2.25 (m, 8H), 1.28-1.10 (m, 6H).

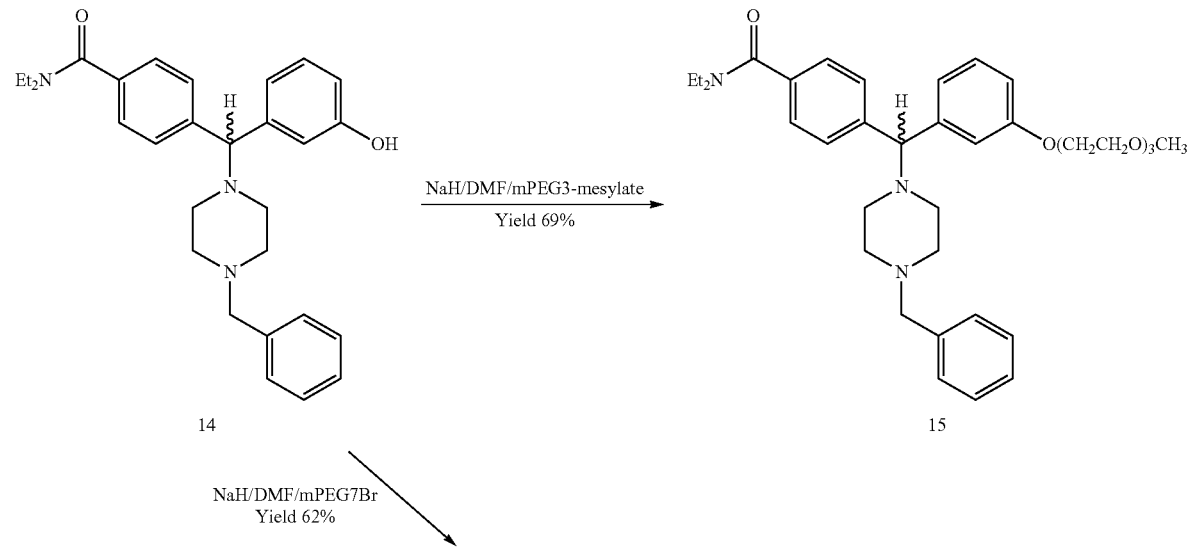

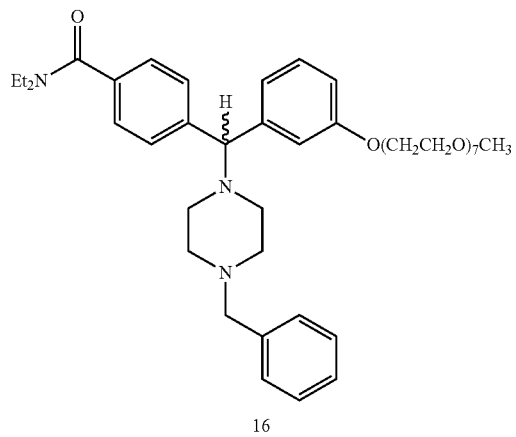

4-[(4-Benzyl-1-piperazinyl)-3-O-methoxy(triethyleneglycol)benzyl]-N,N-diethylbenzamide (15)

Compound 14 (80 mg, 0.18 mmol) was dissolved in anhydrous DMF (10 ml) and NaH (16 mg, 60% in mineral oil, 0.4 mmol) was added to the solution at room temperature. The solution continued to stir at room temperature for 10 minutes at which point, methoxy tri(ethylene glycol) mesylate (105 mg, 0.43 mmol) was added. The reaction solution was stirred at room temperature for 24 hours. Sat. NH$_4$Cl solution (1 ml) was added to the solution. The solvent was removed under reduced pressure and the resulting residue was subjected to flash chromatography (MeOH/DCM=2%~11%) to give a mixture of compound 15 with methoxy tri(ethylene glycol) mesylate as the impurity. The mixture was dissolved in DCM (2 ml). The solution was added to HCl in ethyl ether (1.0 M, 10 ml). Upon addition, a white precipitate appeared and the cloudy solution was centrifuged (4000 rpm, 15 minutes). The clear solvent was removed and the residue in the tube was extracted with Sat. NaHCO$_3$ (5 ml) and DCM (5 ml×3). The organic phases were combined, dried over Na$_2$SO$_4$, filtered, and the solvent removed under reduced pressure to give the desired compound 15 (75 mg, 0.12 mmol, yield 69%). $^1$H NMR (CDCl$_3$): δ 7.43 (d, 2H), 7.31-7.22 (m, 7H), 7.17 (t, 1H), 6.99-6.97 (m, 2H), 6.75-6.72 (m, 1H), 4.20 (s, 1H), 4.10 (t, 2H), 3.87 (t, 2H), 3.75-3.66 (m, 6H), 3.58-3.52 (m, 6H), 3.39 (s, 3H), 3.29-3.23 (m, 2H), 2.55-2.35 (m, 8H), 1.28-1.10 (m, 6H). LC/MS 604 [M+H]$^+$, 626 [M+Na]$^+$.

4-[(4-Benzyl-1-piperazinyl)-3-O-methoxy(heptaethyleneglycol)benzyl]-N,N-diethylbenzamid (16)

Compound 14 (65 mg, 0.15 mmol) was dissolved in anhydrous DMF (10 ml) and NaH (16 mg, 60% in mineral oil, 0.4 mmol) was added to the solution at room temperature. The solution continued to stir at room temperature for 10 minutes at which point, methoxy hepta(ethylene glycol) bromide (80 mg, 0.20 mmol) was added. The reaction solution was stirred at room temperature for 24 hours. Sat. NH$_4$Cl solution (1 ml) was added into the solution. The solvent was removed under reduced pressure and the resulting residue was subjected to flash chromatography (MeOH/DCM=2%~11%) to give a mixture of compound 16 with methoxy hepta(ethylene glycol) bromide as the impurity. The mixture was dissolved in DCM (2 ml). The solution was added to HCl in ethyl ether (1.0 M, 10 ml). Upon addition, a white precipitate appeared and the cloudy solution was centrifuged (4000 rpm, 15 minutes). The clear solvent was removed and the residue in the tube was extracted with Sat. NaHCO$_3$ solution (5 ml) and DCM (5 ml×3). The organic phases were combined, dried with Na$_2$SO$_4$, filtered, and the solvent removed under reduced pressure to give the desired compound 16 (72 mg, 0.09 mmol, yield 62%). $^1$H NMR (CDCl$_3$): δ 7.42 (d, 2H), 7.30-7.22 (m, 7H), 7.13 (t, 1H), 6.98-6.96 (m, 2H), 6.73-6.70 (m, 1H), 4.18 (s, 1H), 4.09 (t, 2H), 3.85 (t, 2H), 3.82-3.62 (m, 22H), 3.56-3.51 (m, 6H), 3.38 (s, 3H), 3.30-3.20 (m, 2H), 2.55-2.35 (m, 8H), 1.28-1.08 (m, 6H). LC/MS 780 [M+H]$^+$, 802 [M+Na]$^+$.

Scheme 5:

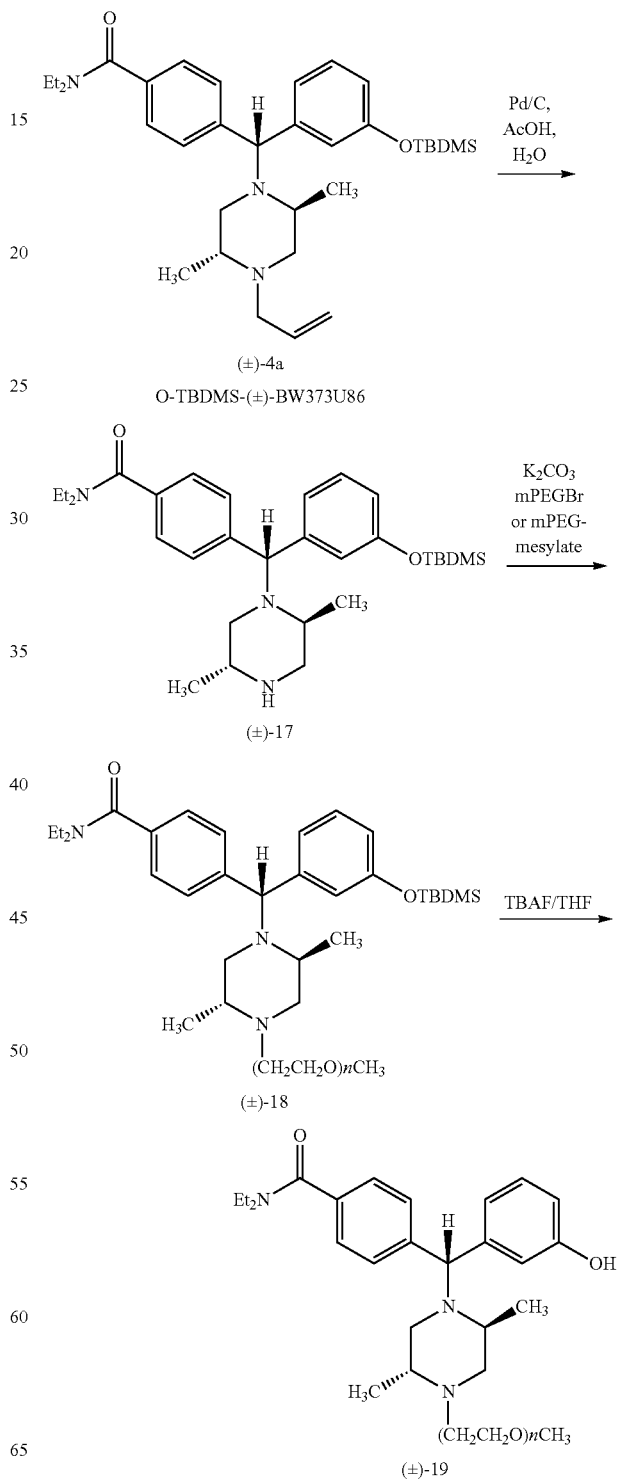

-continued

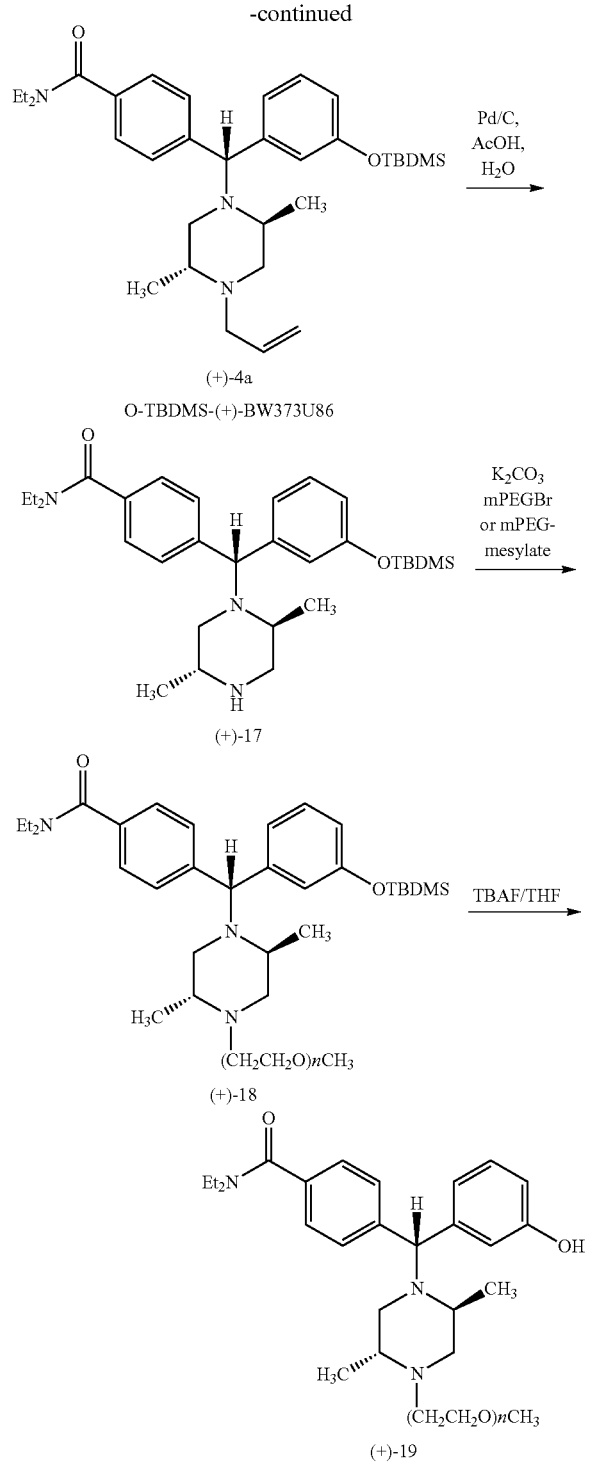

n=3 as example (n may be different monomeric length)

(±)-4-[(αR)-α-((2S,5R)-2,5-dimethyl-1-piperazinyl)-3-O-TBDMS-benzyl]-N,N-diethylbenzamid [(±)-17]

Compound (±)-4-a (0.5 mmol) is mixed with H₂O (6 ml), acetic acid (0.6 ml), and Pd/C (10%, 100 mg). The solution is refluxed for 24 hours. The Pd/C powder is filtered off. The solvent is evaporated in vacuum. The obtained compound (±)-17 is used in the next reaction without further purification.

(±)-4-[(αR)-α-((2S,5R)-4-methoxy(triethylene glycol)-2,5-dimethyl-1-piperazinyl)-3-O-TBDMS-benzyl]-N,N-diethylbenzamide [(±)-18]

Compound (±)-17 (0.4 mmol) is mixed with methoxy tri(ethylene glycol) bromide (0.50 mmol), K₂CO₃ (1.0 mmol) in anhydrous acetonitrile (10 ml). The reaction solution is stirred at 50° C. for 30 minutes. The solid is filtered off and the solvent is evaporated under reduced pressure. The residue is subjected to flash chromatography to give compound (±)-18.

(±)-4-[(αR)-α-((2S,5R)-4-methoxy(triethylene glycol)-2,5-dimethyl-1-piperazinyl)-3-hydroxybenzyl]-N,N-diethylbenzamide [(±)-19]

Compound (±)-18 (0.3 mmol) is mixed with dissolved in THF (10 ml) and TBAF (1.0 M in THF, 0.5 ml) is added to the reaction solution with stirring. The solution continued to stir at room temperature for 3 hours. The solvent is removed under reduced pressure. The resulting residue is subjected to flash chromatography to give compound (±)-19.

The synthesis procedure of (+)-17, (+)-18, and (+)-19 are similar to the synthetic procedures of (±)-17, (±)-18, and (±)-19 as described above. The only difference is using (+)-4-a as starting material instead of (±)-4-a.

Scheme 6:

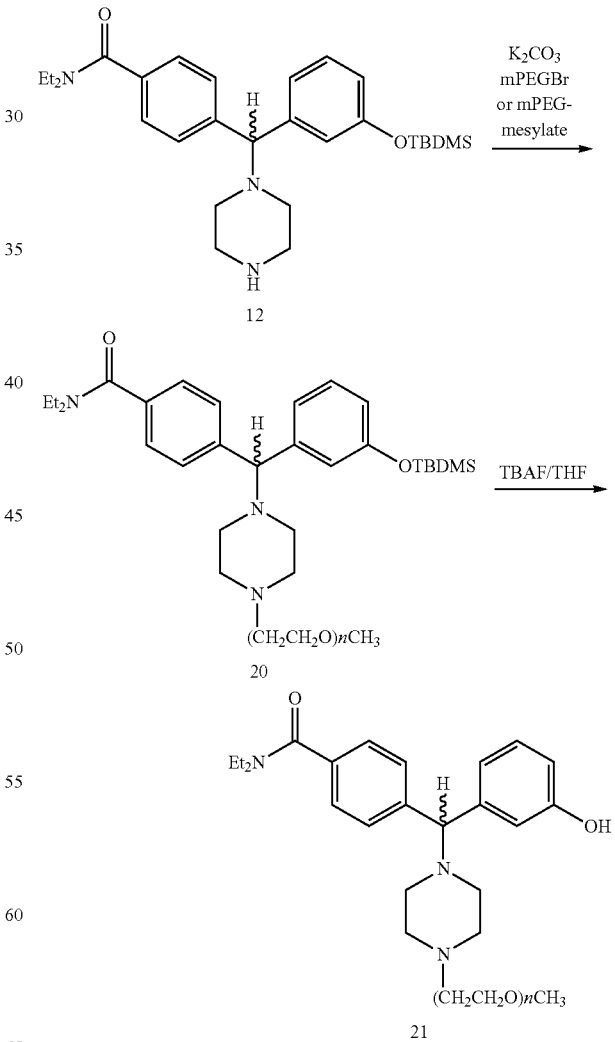

n=3 as example (n may be different monomeric length)

4-[4-methoxy(triethyleneglycol)-1-(piperazinyl)-3-O-TBDMS-benzyl]-N,N-diethylbenzamide (20)

Compound 12 (0.4 mmol) is mixed with methoxy tri(ethylene glycol) bromide (0.50 mmol), K$_2$CO$_3$ (1.0 mmol) in anhydrous acetonitrile (10 ml). The reaction solution is stirred at 50° C. for 30 minutes. The solid is filtered off and the solvent is evaporated under reduced pressure. The resulting residue is subjected to flash chromatography to give compound 20.

4-[4-methoxy(triethyleneglycol)-1-(piperazinyl)-3-hydroxybenzyl]-N,N-diethylbenzamide (21)

Compound 20 (0.3 mmol) is mixed with dissolved in THF (10 ml) and TBAF (1.0 M in THF, 0.5 ml) is added to the reaction solution with stirring. The solution continued to stir at room temperature for 3 hours. The solvent is removed under reduced pressure. The resulting residue is subjected to flash chromatography to give compound 21.

Scheme 7: Synthesis of PEG-BW373U86 Conjugates via Physiologically Stable Linkages:

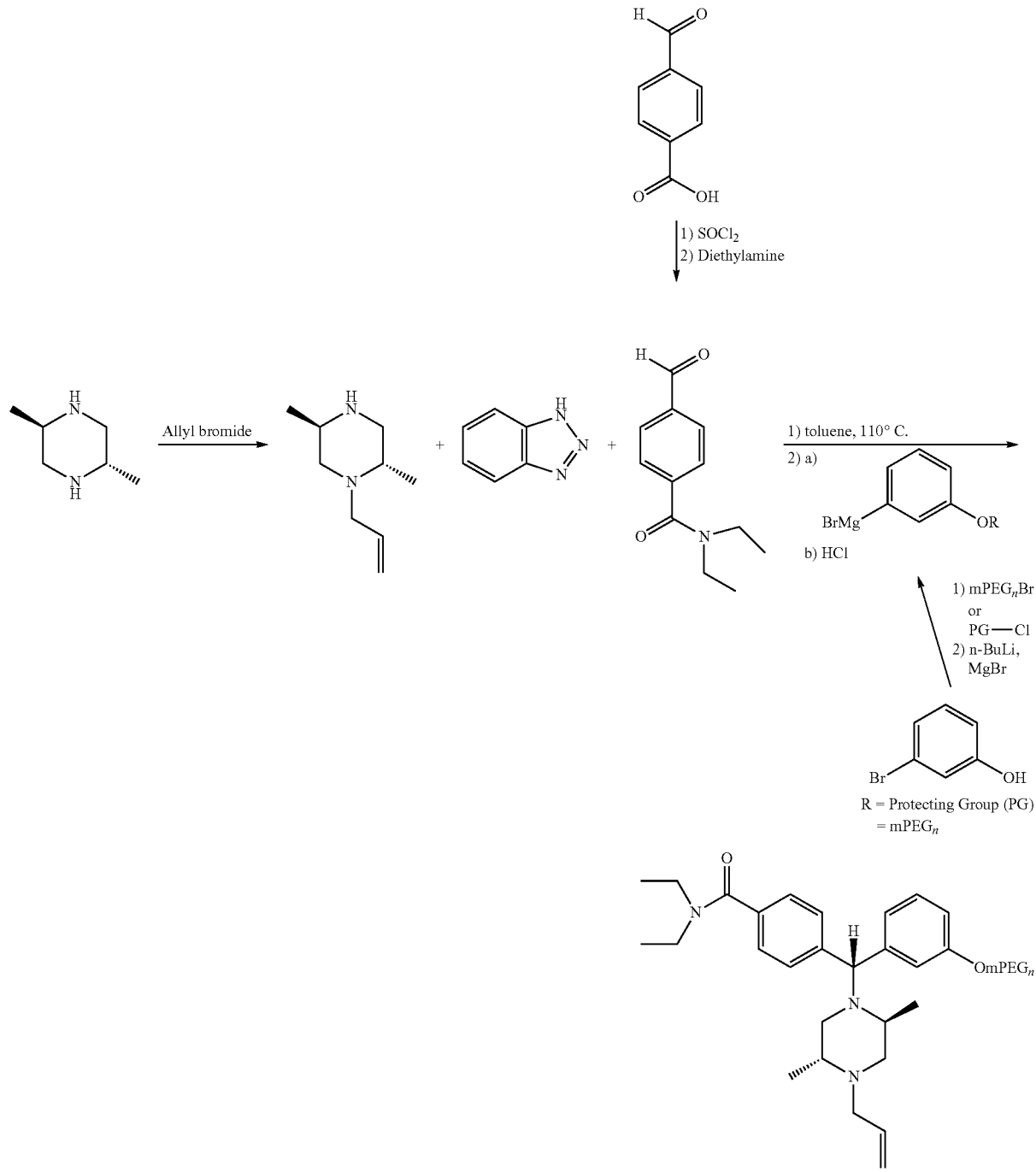

Example 2

Receptor Binding

The binding constants for PEGylated compounds to human δ, κ, and μ, opioid receptors are determined using radioligand competition-binding assays described previously. Test compounds are assayed for inhibition of radioligand binding at final test-compound concentrations ranging between 0.01 μM and 100 μM in half-log increments. Briefly, cell membrane preparations from cells expressing the specific receptor are mixed with a [$^3$H]-labeled tracer (see table, below) and the test compound or a known inhibitor of receptor-ligand binding. Following incubation to allow receptor-ligand complex formation, the complexes are collected by filtration, washed to remove radioligand that was not receptor-bound, and the remaining radioactivity is determined by liquid scintillation counting. Specific radioligand binding is calculated for each test compound concentration and IC$_{50}$ values are determined by a non-linear, least squares regression analysis using MathIQ™ (ID Business Solutions Ltd., UK). Reference standards are run with each assay to ensure the validity of the results. Inhibition constants (K$_i$) were calculated using the equation of Cheng and Prusoff using the observed IC$_{50}$ of the tested compound, the concentration of radioligand employed in the assay and the experimentally determined values for the K$_d$ of the ligand. The Hill coefficient (n$_h$), defining the slope of the competitive binding curve, was calculated using MathIQ™.

| Receptor | Cell source | Radioligand |
|---|---|---|
| Opiate δ | Chinese hamster ovary | [$^3$H]-naltrindole, 0.9 nM |
| Opiate κ | HEK-293 | [$^3$H]-diprenorphine, 0.6 nM |
| Opiate μ | Chinese hamster ovary | [$^3$H]-diprenorphine, 0.6 nM |

Opiate δ: source: Human recombinant (CHO cells)
Ligand: 0.9 nM [$^3$H] Naltrindole
non-specific: 10 μM Naloxone
K$_d$: 0.49 nM
B$_{max}$: 8600 fmol/mg Protein
specific binding 80%
Opiate κ; source: Human recombinant (HEK-293 cells)
Ligand: 0.6 nM [$^3$H] Diprenorphine
Non-specific: 10 μM Naloxone
K$_d$: 0.4 nM
B$_{max}$: 1100 fmol/mg Protein
Specific binding 90%
Opiate μ; Source: Human recombinant CHO-K1 cells
Ligand: 0.6 nM [.$^3$H] Diprenorphine
Vehicle: 1% DMSO
Incubation Time/Temp: 60 minutes @ 25.0
Incubation Buffer: 50 mM Tris-HCl, pH 7.4
K$_d^1$: 0.41 nM*
B$_{MAX}$: 3.8 pmole/mg Protein*
Non-Specific Ligand: 10 μM Naloxone
Specific Binding: 90%*
For all: Significance Criteria: >=50% of max stimulation or inhibition
Quantitation Method Radioligand Binding

TABLE 1

| Molecule | Opiate δ, Ki (nM) | Fold change |
|---|---|---|
| ±BW373U86 | 0.44, 0.36 | 1 |
| mPEG-3 ± BW373U86 | ~415.4 | ~98 |
| mPEG-7 ± BW373U86 | ~1330 | ~298 |
| mPEG-3 ± BW373U86 | 491 | 137.23 |
| mPEG-7 ± BW373U86 | 863.5 | 242.7 |

TABLE 2

| Compound | Opiate Receptor, delta | | (OP1, DOP) | | | |
|---|---|---|---|---|---|---|
| | IC$_{50}$, nM | SEM | Ki, nM | SEM | nH | SEM |
| mPEG$_3$-O-(+)BW373U86 | 723 | 55 | 255 | 20 | 0.95 | 0.19 |
| (+) BW373U86 | 1 | 0.083 | 0.354 | 0.029 | 0.91 | 0.07 |
| demethyl-BW373U86 | 7.09 | 1.05 | 2.5 | 0.368 | 1.10 | 0.17 |
| mPEG$_3$-demethyl-BW373U86 | 6050 | 641 | 2130 | 226 | 1.01 | 0.16 |
| mPEG$_7$-demethyl-BW373U86 | 3470 | 820 | 1220 | 289 | 0.85 | 0.02 |
| N-benzyl-deallyl-demethyl-BW373U86 | 1.33 | 0.131 | 0.47 | 0.046 | 0.99 | 0.04 |
| mPEG$_3$-N-benzyl-deallyl-demethyl-BW373U86 | 212 | 19 | 74.7 | 7 | 1.50 | 0.09 |
| mPEG$_7$-N-benzyl-deallyl-demethyl-BW373U86 | 106 | 6 | 37.4 | 2 | 1.08 | 0.03 |
| (+/−) BW373U86 dihydrobromide | 3.26 | 0.613 | 1.15 | 0.216 | 1.05 | 0.12 |
| mPEG3-N-(+/−)-BW373U86 | 764 | 176 | 269 | 62 | 0.95 | 0.04 |
| mPEG7-N-(+/−)-BW373U86 | 2090 | 308 | 735 | 108 | 1.22 | 0.19 |

TABLE 3

| Compound | Opiate Receptor, kappa | | (OP2, KOP) | | | |
|---|---|---|---|---|---|---|
| | $IC_{50}$, nM | SEM | Ki, nM | SEM | nH | SEM |
| mPEG$_3$-O-(+)BW373U86 | ND | ND | ND | ND | ND | ND |
| (+) BW373U86 | 223 | 48 | 89.2 | 19 | 0.78 | 0.04 |
| demethyl-BW373U86 | 1000 | 61 | 401 | 24 | 0.87 | 0.03 |
| mPEG$_3$-demethyl-BW373U86 | ND | ND | ND | ND | ND | ND |
| mPEG$_7$-demethyl-BW373U86 | ND | ND | ND | ND | ND | ND |
| N-benzyl-deallyl-demethyl-BW373U86 | 2370 | 274 | 946 | 110 | 0.95 | 0.09 |
| mPEG$_3$-N-benzyl-deallyl-demethyl-BW373U86 | ND | ND | ND | ND | ND | ND |
| mPEG$_7$-N-benzyl-deallyl-demethyl-BW373U86 | ND | ND | ND | ND | ND | ND |
| (+/−) BW373U86 dihydrobromide | 556 | 84 | 223 | 34 | 0.92 | 0.14 |
| mPEG3-N-(+/−)-BW373U86 | ND | ND | ND | ND | ND | ND |
| mPEG7-N-(+/−)-BW373U86 | ND | ND | ND | ND | ND | ND |

TABLE 4

| Compound | Opiate Receptor, μ | | (OP3, MOP) | | | |
|---|---|---|---|---|---|---|
| | $IC_{50}$, nM | SEM | Ki, nM | SEM | nH | SEM |
| mPEG$_3$-O-(+)BW373U86 | | | | | | |
| (+) BW373U86 | 309 | 35 | 126 | 14 | 0.83 | 0.05 |
| demethyl-BW373U86 | 11000 | 216 | 4450 | 88 | 1.02 | 0.02 |
| mPEG$_3$-demethyl-BW373U86 | ND | ND | ND | ND | ND | ND |
| mPEG$_7$-demethyl-BW373U86 | ND | ND | ND | ND | ND | ND |
| N-benzyl-deallyl-demethyl-BW373U86 | 2750 | 206 | 1110 | 83 | 0.90 | 0.06 |
| mPEG$_3$-N-benzyl-deallyl-demethyl-BW373U86 | ND | ND | ND | ND | ND | ND |
| mPEG$_7$-N-benzyl-deallyl-demethyl-BW373U86 | ND | ND | ND | ND | ND | ND |
| (+/−) BW373U86 dihydrobromide | 659 | 18 | 268 | 7 | 0.92 | 0.04 |
| mPEG3-N-(+/−)-BW373U86 | 9370 | 243 | 3810 | 99 | 1.14 | 0.03 |
| mPEG7-N-(+/−)-BW373U86 | ND | ND | ND | ND | ND | ND |

What is claimed is:

1. A compound having a structure selected from the group consisting of

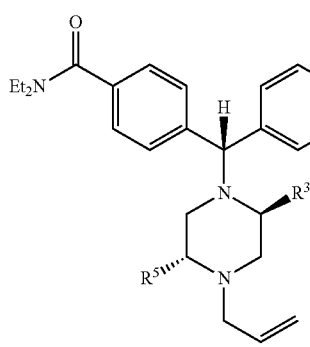

and

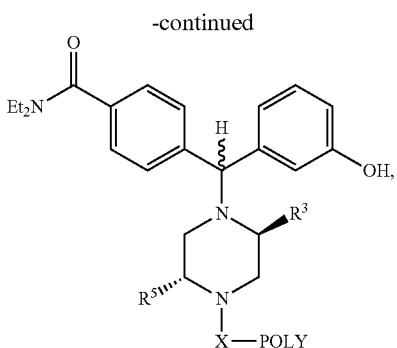

wherein, in each structure, $R^3$ is either H or $CH_3$, $R^5$ is either H or $CH_3$, X is a spacer moiety, and POLY is a water-soluble, non-peptidic oligomer.

2. The compound of claim 1, wherein the water-soluble, non-peptidic oligomer is a poly(alkylene oxide).

3. The compound of claim 2, wherein the poly(alkylene oxide) is a poly(ethylene oxide).

4. The compound of claim 1, wherein the water-soluble, non-peptidic oligomer has between 1 and 30 monomers.

5. The compound of claim 4, wherein the water-soluble, non-peptidic oligomer has between 1 and 10 monomers.

6. The compound of claim 2, wherein the poly(alkylene oxide) includes an alkoxy or hydroxy end-capping moiety.

7. The compound of claim 1, wherein the water-soluble, non-peptidic oligomer is covalently attached via a stable linkage.

8. The compound of claim 1, wherein the water-soluble, non-peptidic oligomer is covalently attached via a degradable linkage.

9. The compound of claim 1, wherein X is an oxygen.

10. The compound of claim 1, wherein X is an ester.

11. A composition comprising a compound of claim 1, and optionally, a pharmaceutically acceptable excipient.

12. A composition of matter comprising a compound of claim 1, wherein the compound is present in a dosage form.

* * * * *

UNITED STATES PATENT AND TRADEMARK OFFICE
CERTIFICATE OF CORRECTION

PATENT NO. : 8,685,979 B2  Page 1 of 1
APPLICATION NO. : 12/864481
DATED : April 1, 2014
INVENTOR(S) : Ren et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 826 days.

Signed and Sealed this
Thirtieth Day of May, 2017

Michelle K. Lee
*Director of the United States Patent and Trademark Office*